United States Patent
Dalai et al.

(10) Patent No.: US 6,495,356 B1
(45) Date of Patent: Dec. 17, 2002

(54) BERYLLOFLUORIDE ANALOGUES OF ACYL PHOSPHATE POLYPEPTIDES

(75) Inventors: Yan Dalai, Albany, CA (US); Sydney Kustu, Berkeley, CA (US); Ho S. Cho, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/705,233

(22) Filed: Nov. 1, 2000

Related U.S. Application Data

(60) Provisional application No. 60/168,431, filed on Nov. 30, 1999.

(51) Int. Cl.[7] .................................................. C12N 9/12
(52) U.S. Cl. ....................................................... 435/194
(58) Field of Search ......................................... 435/194

(56) References Cited

PUBLICATIONS

Werber et al., Characterization of stable beryllium fluoride, aluminum fluoride and vanadate containing myosin subfragment 1–nucleotide complexes (1992) Biochemistry, vol. 31, pp. 7190–7197.*

Henry et al., Observation of multiple myosin subfragment 1–ADP–fluoroberyllate complexes by 19F NMR spectroscopy (Oct. 5, 1993) Biochemistry, vol. 32, pp. 10451–10456.*

Phan et al., Complexes of myosin subfragment–1 with adenosine diphosphate and phosphate analogs: probes of active site protein conformation, (1996) Biophysical Chemistry ,vol. 59, pp. 341–349.*

Peinnequin et al., Does pyrophosphate bind the catalytic sites of mitrocondrial F1–ATPase? (1992) Biochemistry, vol. 31, pp. 2088–2092.*

Maruta et al., Formation of the stable myosin–ADP–aluminum fluoride and myosin–ADP–beryllium fluoride complexes and their analysis using 19F NMR (1993) Biochemistry, vol. 268, No. 10, pp. 7093–7100.*

Carlier et al., Stabilization of microtubules by inorganic phosphate and its structural analogues, the fluoride complexes of aluminum and beryllium (1988) Biochemistry, vol. 27, pp. 3555–3559.*

Moreau et al., RecA protein–promoted cleavage of lexa repressor in the presence of ADP and structural analogues of inorganic phosphate, the fluoride complexes of alumunum and beryllium (1989) Biochemistry, vol. 264, No. 4, pp. 2302–2306.*

(List continued on next page.)

Primary Examiner—Jon P. Weber
(74) Attorney, Agent, or Firm—Bozicevic, Field and Francis LLP; Carol L. Francis

(57) ABSTRACT

The present invention features methods and compositions for production of persistent acyl phosphate analogues (e.g., aspartyl phosphate analogues) using beryllofluoride ($BeF_x$), as well as polypeptides comprising such an acyl phosphate analogue and antibodies that specifically bind to these polypeptides. The invention further features methods of using BeFx analogues in screening assays to identify candidate agent compounds that modulate activity of polypeptides that normally exhibit activity due to the presence of an acyl phosphate linkage (e.g., a phosphorylated aspartate residue as in, e.g., polypeptides involved in signal transduction, polypeptides involved in ion transport across biological membranes, phosphotransferases, etc.). The BeFx polypeptide analogues can also be used to facilitate determination of the structure of the corresponding phosphorylated polypeptide and in rationale drug design.

15 Claims, 13 Drawing Sheets

OTHER PUBLICATIONS

Maruta et al., Analysis of stress in the active site of myosin accompanied by conformational changes in the transient state intermediate complexes using photoaffinity labeling and 19F–NMR spectroscopy (May 15, 1998) Eur. J. Biochem , vol. 252, pp. 520–529.*

Halkides et al., Synthesis and biochemical characterization of an analoge of CheY–phosphate, a signal transduction protein in bacterial chemotaxis (Sep. 5, 1998) Biochemistry, vol. 37, pp. 13674–13680.*

Clarke et al., *Klebsiella pneumoniae* nitrogenase: formation and stability of putative beryllium fouride–ADP transition state complexes (Jul. 14, 1999) Biochemistry, vol. 38, pp. 9906–9913.*

Aravind et al. (1998) "The catalytic domain of the P–type ATPase has the haloacid dehalogenase fold." *TIBS*, vol. 23: 127–129.

Baikalov et al. (1996) "Structure of the *Escherichia coli* Response Regulator NarL." *Biochemistry*, vol. 35:11053–11061.

Chabre (1990) "Aluminofluoride and beryllofluoride complexes: new phosphate analogs in enzymology." *TIBS*, vol. 15:6–10.

Collet et al. (1998) "A New Class of Phosphotransferases Phosphorylated on an Aspartate Residue in an Amino–terminal DXDX(T/V) Motif." *The Journal of Biological Chemistry*, vol. 273(23):14107–14112.

Collet et al. (1997) "Human L–3–phosphoserine phosphatase: sequence, expression and evidence for a phosphoenzyme intermediate." *Febs Letters*, vol. 408:281–284.

Di Sabato et al. (1961) "Mechanism and Catalysis of Reactions of Acyl Phosphates. II. Hydrolysis."*J. Am. Chem. Soc.,* vol. 83:4400–4405.

Djordjevic et al. (1998) "Structural basis for methylesterase CheB regulation by a phosphorylation–activated domain." *Proc. Natl. Acad. Sci. USA,* vol. 95:1381–1386.

Drake et al. (1993) "Activation of the Phosphosignaling Protein CheY." *The Journal of Biological Chemistry*, vol. 268(18):13081–13088.

Drummond et al. (1986) "Sequence and domain relationships ntrC and nifA from *Klebsiella pneumoniae:* homologies to other regulatory proteins." *The EMBO Journal*, vol. 5(2):441–447.

Dziejman et al. (1995) "Two–Component Signal Transduction and its Role in the Expression of Bacterial Virulence Factors." *Two–component signal transduction,* eds Hoch and Silhavy, (ASM, Washington D.C), pp. 305–317.

Fabret et al. (1999) "Two–Component Signal Transduction in *Bacillus subtilis:* How One Organism Sees Its World." *Journal of Bacteriology,* vol. 181(7):1975–1983.

Feher et al. (1997) "High–Resolution NMR Structure and Backbone Dynamics of the *Bacillus subtilis* Response Regulator, SpoOF: Implications for Phosphorylation and Molecular Recognition." *Biochemistry*, vol. 36:10015–10025.

Groisman (1998) "The ins and outs of virulence gene expression: $Mg^{2+}$ as a regulatory signal." *BioEssays*, vol. 20:96–101.

Haldimann et al. (1997) "Transcriptional Regulation of the *Enterococcus faecium* BM4147 Vancomycin Resistance Gene Cluster by the VanS–VanR Two–Component Regulatory System in *Escherichia coli* K–12." *Journal of Bacteriology,* vol. 179(18):5903–5913.

Hunter (1991) "Protein Kinase Classification." *Methods in Enzymology*, vol. 200:3–37.

Koonin et al. (1994) "Computer Analysis of Bacterial Haloacid Dehalogenases Defines a Large Superfamily of Hydrolases with Diverse Specificity." *J. Mol. Biol.,* vol. 244:125–132.

Koshland, Jr. (1952) "Effect of Catalysts on the Hydrolysis of Acetyl Phosphate. Nucleophilic Displacement Mechanisms in Enzymatic Reactions." *J. Am. Chem. Soc.,* vol. 74:2286–2292.

Li et al. (1999) "Mutations Affecting Motifs of Unknown Function in the Central Domain of Nitrogen Regulatory Protein C." *Journal of Bacteriology,* vol. 181(17):5443–5454.

Lowry et al. (1994) "Signal Transduction in Chemotaxis." *The Journal of Biological Chemistry,* vol. 269(42):26358–26362.

MacLennan et al. (2000) "Pumping ions." *Nature,* vol. 405:633–634.

Maeda et al. (1994) "A two–component system that regulates an osmosensing MAP kinase cascade in yeast." *Nature,* vol. 369:242–245.

Magasanik (1996) "Regulation of Nitrogen Assimilation." *Regulation of gene expression in E–coli,* eds. Linand Lynch (R.G. Landes Co., Austin), pp. 281–290.

Mizuno (1997) "Compilation of All Genes Encoding Two–component Phosphotransfer Signal Transducers in the Genome of *Escherichia coli.*" *DNA Research,* vol. 4:161–168.

Mizuno et al. (1996) "Compilation of All Genes Encoding Bacterial Two–component Signal Transducers in the Genome of the Cyanobacterium, Synechocystis sp. Strain PCC 6803." *DNA Research,* vol. 3:407–414.

Morett et al. (1993) "The $\sigma^{54}$ Bacterial Enhancer–Binding Protein Family: Mechanism of Action and Phylogenetic Relationship of Their Functional Domains." *Journal of Bacteriology,* vol. 175(19):6067–6074.

Ninfa et al. (1986) "Covalent modification of the glnG product, $NR_I$, by the glnL product, $NR_{II}$, regulates the transcription of the glnALG operon in *Escherichia coli.*" *Proc. Natl. Acad. Sci. USA,* vol. 83:5909–5913.

Ninfa et al. (1995) "Control of Nitrogen Assimillation by the $NR_I$–$NR_{II}$ Two–Component System for Enteric Bacteria." *Two–Component Signal Transduction,* eds. Hoch and Silhavy (ASM, Washington, D.C.) pp. 67–88.

Nixon et al. (1986) "Two–component regulatory systems responsive to environmental stimuli share strongly conserved domains with the nitrogen assimilation regulatory genes ntrB and ntrC." *Proc. Natl. Acad. Sci. USA,* vol. 83:7850–7854.

Nohaile et al. (1997) "Structural and Functional Analyses of Activating Amino Acid Substitutions in the receiver Domain of NtrC: Evidence for an Activating Surface." *J. Mol. Biol.,* vol. 273:299–316.

North et al. (1993) "Prokaryotic Enhancer–Binding Proteins Reflect Eukaryote–Like Modularity: the Puzzle of Nitrogen Regulatory Protein C." *Journal of Bacteriology,* vol. 175(14):4267–4273.

Novak et al. (1999) "Emergence of vancomycin tolerance in *Streptococcus pneumoniae."* *Nature,* vol. 399:590–593.

Osuna et al. (1997) "A proposed architecture for the Central domain of the bacterial enhancer–binding proteins based on secondary structure prediction and fold recognition." *Protein Science,* vol. 6:543–555.

Ota et al. (1993) "A Yeast Protein Similar to Bacterial Two–Component Regulators." *Science*, vol. 262:566–569.

Parkinson et al. (1992) "Communication Modules in Bacterial Signaling Proteins." *Annu. Rev. Genet.*, vol. 26:71–112.

Pirard et al. (1997) "Comparison of PMM1 with the phosphomannomutases expressed in rat liver and in human cells." *FEBS Letters*, vol. 411:251–254.

Porter et al. (1995) "Mechanism of Transcriptional Activation by NtrC." *Two–Component Signal Transduction*, eds. Hoch and Silhavy, T.J. (ASM, Washington, D.C.), pp. 147–158.

Porter et al. (1993) "Oligomerization of NTRC at the glnA enhancer is required for transcriptional activation." *Genes & Development*, vol. 7: 2258–2273.

Quon et al. (1996) "Cell Cycle Control by an essential Bacterial Two–Component signal Transduction Protein." *Cell*, vol. 84:83–93.

Rombel et al. (1998) "The Bacterial Enhancer–Binding Protein NtrC as a Molecular Machine." *Cold Spring Harbor Symposia on Quantitative Biology*, vol. LXIII: 157–165.

Ruis et al. (1995) "Stress signaling in yeast." *BioEssays*, vol. 17(11):959–965.

Schaller (1997) "Ethylene and cytokinin signaling in plants: the role of two–component systems." *Essays Biochem.* vol. 32:101–111.

Seal et al. (1987) "Characterization of a Phosphoenzyme Intermediate in the Reaction of Phosphoglycolate Phosphatase." *The Journal of Biological Chemistry*, vol. 262(28):13496–13500.

Silversmith et al. (1999) "Throwing the switch in bacterial chemotaxis." *Trends in Microbiology*, vol. 7(1):16–22.

Sola et al. (1999) "Three–dimensional Crystal Structure of the Transcription Factor PhoB Receiver Domain." *J. Mol. Biol.*, vol. 285:675–687.

Stock et al. (1989) "Three–dimensional structure of CheY, the response regulator of bacterial chemotaxis." *Nature*, vol. 337:745–749.

Stock et al. (1995) "Two–Component Signal Transduction Systems: Structure–Function Relationships and Mechanisms of Catalysis." *Two–component signal transduction*, eds. Hoch and Silhavy, T.J. (ASM, Washington D.C.) pp 25–51.

Volkman et al. (1995) "Three–Dimensional Solution Structure of the N–Terminal receiver Domain of NTRC." *Biochemistry*, vol. 34:1413–1424.

Wanner (1995) "Signal Transduction and Cross Regulation in the *Escherichia coli* Phosphate Regulon by PhoR, CreC, and Acetyl Phosphate." *Two–component signal transduction*, eds. Hoch and Silhavy, T.J. (ASM, Washington D.C.) pp 25–51.

Wyman et al. (1997) "Unusual Oligomerization Required for activity of NtrC, a Bacterial Enhancer–Binding Protein." *Science*, vol. 275:1658–1661.

Cho et al. (2000) "NMR Structure of Activated CheY", *J. Mol. Biol.*, vol. 297(3):543–51.

Murphy et al. (1993) "Formation of A Stable Inactive Complex of the Sarcoplasmic Reticulum Calcium ATPase with Magnesium, Beryllium, and Fluoride." *The Journal of Biological Chemistry*, vol. 268(31):23307–23310.

Petsko (2000) "Chemistry and biology" *PNAS*, vol. 97(2): 538–540.

Robinson et al. (1986) "Fluoride and Beryllium Interact with the (Na + K)–Dependent ATPase as Analogs of Phosphate." *Journal of Bioenergetics and Biomembranes*, vol. 18(6): 521–531.

Tiruppathi et al. (2000) "G protein–coupled receptor kinase–5 regulates thrombin–activated signaling in endothelial cells." *PNAS*, vol. 97(13):7440–7445.

Yan et al. (1999) "Beryllofluoride mimics phosphorylation of NtrC and other bacterial response regulators." *PNAS*, vol. 96(26):14789–14794.

Murphy et al. (1993) "Formation of a Stable Inactive Complex of the Sarcoplasmic Reticulum Calcium ATPase with Magnesium, Beryllium, and Fluoride." *The Journal of Biological Chemistry*, vol. 268(81) :28807–28810.

Murphy et al. (1992) "Fluoride is a Slow, Tight–binding Inhibitor of the Calcium ATPase of Sarcoplasmic Reticulum." *The Journal of Biological Chemistry*, vol. 267(8) : 5229–5235.

* cited by examiner

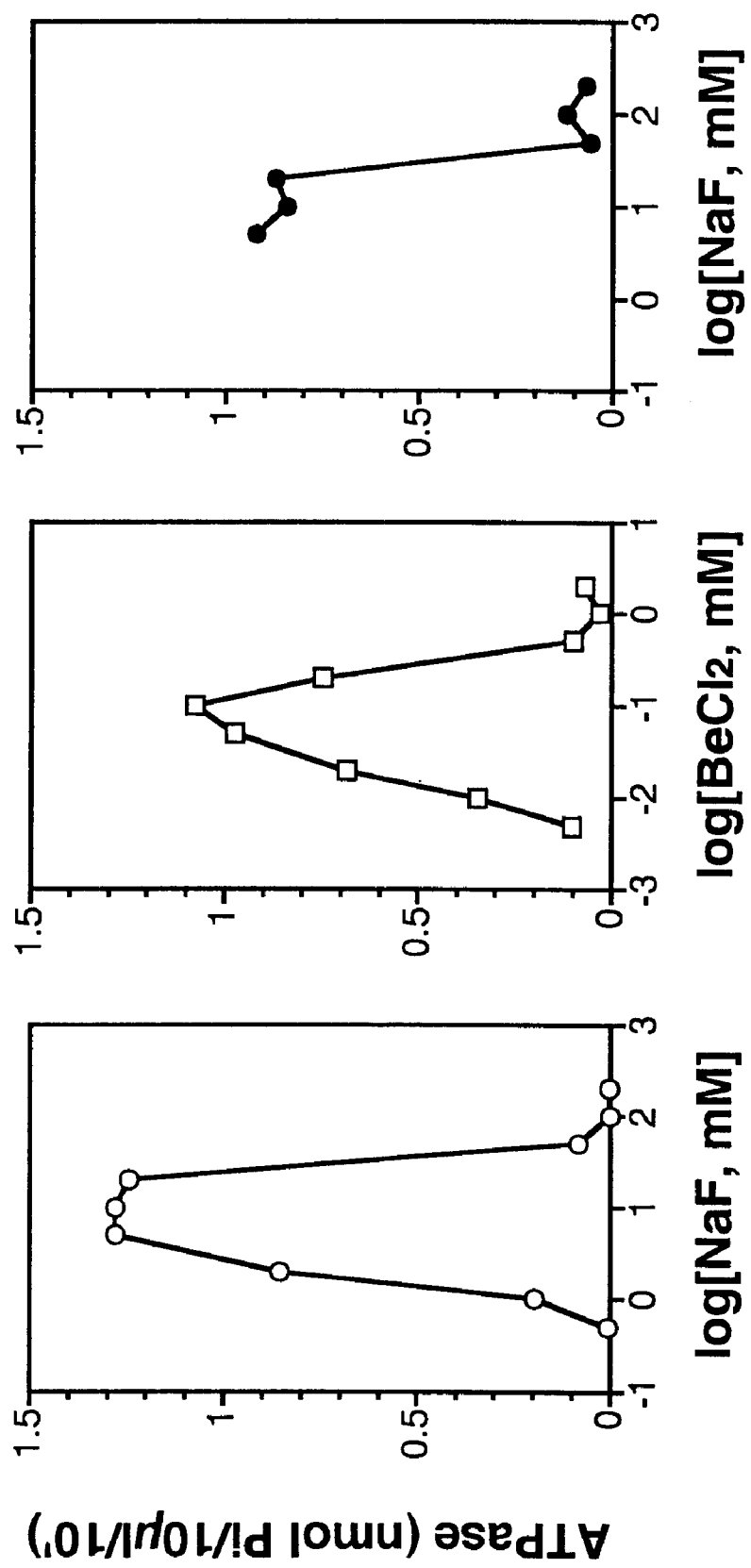

P-Asp

BeF₃·Asp

US 6,495,356 B1

BERYLLOFLUORIDE ANALOGUES OF ACYL PHOSPHATE POLYPEPTIDES

CROSS-REFERENCE TO RELATED APPLICATIONS

This application claims the benefit of U.S. Provisional Application No. 60/168,431, Filed Nov. 30, 1999, which application is incorporated herein by reference.

STATEMENT AS TO FEDERALLY SPONSORED RESEARCH

This invention was made, at least in part, with a government grant from the National Institutes of Health (Grant Nos. NIH grants GM38361). The U.S. government may have certain rights in this invention.

FIELD OF THE INVENTION

The invention relates generally to acyl phosphate analogues, particularly to aspartyl phosphate analogues, as well as methods of their production and use.

BACKGROUND OF THE INVENTION

Phosphorylation is a frequent covalent modification that proteins undergo in a post-translational process, and a fundamental dynamic event in a large array of cellular functions. Based on the phosphorylated amino acid residue, several groups can be classified (Hunter (1991) *Methods in Enzymology* 200, 3–37): 1) phosphoesters on serine, threonine and tyrosine; 2) phosphothioester on cysteine; 3) phosphoramidates on histidine, arginine and lysine; and 4) phosphate acid anhydrides on aspartate and glutamnate. Unlike the others, the last type of bond is highly unstable—the half-life of an acyl phosphate linkage is just hours under physiological conditions (Koshland (1951) *J. Am. Chem. Soc.* 74, 2286–2292; Di Sabato et al. (1961) *J. Am. Chem. Soc.* 83, 4400–4405). Protein phosphorylation on an aspartate residue occurs widely. For example, phosphorylation on aspartate residues occurs in two large protein families—response regulators and the haloacid dehalogenase (HAD) superfamily of hydrolases.

Response regulators, together with their cognate autokinases, dominate signal transduction in the bacteria (Nixon et al. (1986) *Proc. Natl. Acad. Sci. USA* 83, 7850–7854; Parkinson and Kofoid (1992) *Annu. Rev. Genet.* 26, 71–112; Stock et al (1995) in *Two-component signal transduction*, eds. Hoch and Silhavy, T. J. (ASM, Washington, D.C.), pp. 25–51; Mizuno et al. (1996) *DNA Res.* 3, 407–414.; Mizuno (1997) *DNA Res.* 4, 161–168) and are also found upstream of protein kinase cascades in eukarya (Ota et al. (1993) *Science* 262, 566–569; Maeda et al. (1994) *Nature* (London) 369, 242–245; Ruis and Sch üiller (1995) *BioEssays* 17, 959–965; Schaller (1997) *Essays Biochem.* 32, 101–111). Autokinase/response regulator pairs, which are referred to as "two-component" systems, control bacterial cell division (Quon et al. (1996) *Cell* 84, 83–93), development (Fabret et al. (1999) *J. Bacteriol.* 181, 1975–1983), chemotaxis (Silversmith and Bourret (1999) *Trends MicrobioL* 7, 16–22), virulence (Dziejman and Mekalanos (1995) in *Two-component signal transduction*, eds. Hoch and Silhavy, (ASM, Washington, D.C.), pp. 305–317; Haldimann et al. (1997) *J. Bacteriol* 179, 5903–5913; Groisman (1998) BioEssays 20, 96–101; Novak et al. (1999) *Nature* (London) 399, 590–593), and the responses to many changes in nutrient availability (Ninfa et al. (1995) in *Two-Component Signal Transduction*, eds. Hoch and Silhavy (ASM, Washington, D.C.), pp. 67–88; Wanner (1995) in *Two-Component Signal Transduction*, eds. Hoch and Silhavy (ASM, Washington, D.C.), pp. 203–221). In general, phosphorylation of an aspartate residue in receiver domains of response regulators is used to modulate the function of their corresponding output domains (Ninfa and Magasanik (1986) *Proc. Natl. Acad. Sci. USA* 83, 5909–5913), many of which activate or repress transcription (Parkinson and Kofoid (1992) *Annu. Rev. Genet.* 26, 71–112; Stock et al. (1995) in *Two-component signal transduction*, eds. Hoch and Silhavy, T. J. (ASM, Washington, D.C.), pp. 25–51).

The structures of six unphosphorylated receiver domains have been determined (Stock et al. (1989) *Nature* (London) 337, 745–749; Volkman et al. (1995) *Biochemistry* 34, 1413–1424; Baikalov et al. (1996) *Biochemistry* 35, 11053–11061; Feher et al. (1997) *Biochemistry* 36, 10015–10025; Djordjevic et al. (1998) *Proc. Natl. Acad. Sci. USA* 95, 1381–1386; Sola et al. (1999) *J. Mol Biol.* 285, 675–687) and it has been shown that a substantial conformational change occurs upon phosphorylation in several cases (Drake et al. (1993) *J. Biol. Chem.* 268, 13081–13088; Lowry et al. (1994) *J. Biol Chem.* 269, 26358–26362; Nohaile et al. (1997) J. Mol. Biol. 273, 299–316). However, the lability of the acyl phosphate linkages in these domains (half lives of seconds to hours) (Parkinson and Kofoid (1992) *Annu. Rev. Genet.* 26, 71–112; Stock et al. (1995) in *Two-component signal transduction*, eds. Hoch and Silhavy, T. J. (ASM, Washington, D.C.), pp. 25–51) has hindered structural studies of their phosphorylated, active forms.

The response regulator NtC (nitrogen regulatory protein C), an enhancer-binding protein, functions as a molecular machine to activate transcription by the $\sigma^{54}$-holoenzyme form of RNA polymerase (Magasanik (1996) in *Regulation of gene expression in Escherichia coli*, eds. Linand Lynch (R. G. Landes Co., Austin), pp. 281–290; Rombel et al. (1998) *Cold Spring Harbor Symp. Quant. Biol.* 63, 157–166; Porter et al. (1995) in *Two-component signal transduction*, eds. Hoch and Silhavy, T. J. (ASM, Washington, D.C.), pp. 147–158). The NtrC protein of *Salmonella typhimurium* is composed of three functional domains (Drummond et al. (1986) *EMBO J.* 5, 441–447; North et al. (1993) *J. Bacteriol.* 175, 4267–4273; Morett and Segovia (1993) *J. Bacteriol.* 175, 6067–6074): an amino (N)-terminal receiver or regulatory domain that is phosphorylated on aspartate 54 (D54), a central output domain that hydrolyzes ATP and activates transcription, and a C-terminal DNA-binding domain. The central domain of NtrC apparently adopts a mononucleotide-binding fold characteristic of a large group of purine nucleotide-binding proteins (Osunan et al. (1997) *Protein Sci.* 6, 543–555; Li et al. (1999) *J. Bacteriol.* 181, 5443–5454). Phosphorylation of D54 allows NtrC to form large oligomers that are essential for ATP hydrolysis and hence transcriptional activation (Rombel et al. (1998) *Cold Spring Harbor Symp. Quant. Biol.* 63, 157–166; Porter et al. (1995) in *Two-component signal transduction*, eds. Hoch and Silhavy (ASM, Washington, D.C.), pp. 147–158; Porter et al. (1993) *Genes Dev.* 7,2258–2273; Wyman et al. (1997) *Science* 275, 1658–1661).

Despite the importance of the protein in transcriptional regulation, the receiver domain of NtrC (NtrC$^r$) is the only such domain for which the structures of both the phosphorylated and unphosphorylated forms have been determined (Volkman et al. (1995) *Biochemistry* 34, 1413–1424). Although it was possible to maintain phosphorylated NtrC$^r$ (P-NtrC$^r$) for long enough to allow determination of its structure by NMR spectroscopy, methods for doing so and for collecting and analyzing the necessary data were nontrivial.

The members of the HAD superfamily of hydrolases, which have diverse specificity (Koonin, E. V., et al., (1994) *Journal of Molecular Biology* 244, 125–132; Aravind, L., et al., (1998) *Trends in Biochemical Sciences* 23, 127–129), are examples of other important aspartate-phosphorylated proteins. Whereas 2-haloacid dehalogenase, the founding member of this large protein family, does not catalyze hydrolysis of phosphate substrates nor depend on $Mg^{2+}$, most other members do. Among them, a phosphotransferase subgroup includes several phosphatases, such as phosphoserine phosphatase (PSP), and some forms of phosphomutases. Another subgroup is composed of the P-type ATPases. These proteins play a major role in ion transport across biological membranes (MacLennan et al. (2000) *Nature* 405, 633–634). Phospho-enzyme by intermediates have been detected in phosphotransferases (Seal, S. N., et al., (1987) *Journal of Biological Chemistry* 262, 13496–13500; Pirard, M., et al., (1997) *Febs Letters* 411, 251–254; Collet, J. F., et al., (1997) *Febs Letters* 408, 281–284; Collet, J. F., et al., (1998) *Journal of Biological Chemistry* 273, 14107–14112), and it is also well known that a phospho-intermediate forms during the action of P-type ATPases (MacLennan et al. (2000) *Nature* 405, 633–634) In both cases, phosphorylation requires $Mg^+$ and occurs at a conserved aspartate residue.

Aluminofluoride and beryllofluoride are phosphate analogs for many purine nucleotide binding proteins, such as G proteins, FI-ATPase, myosin, and nitrogenase (see, e.g., Chabre (1990) *Trends Biochem. Sci.* 15, 6–10; Petsko (2000) *Proceedings of the National Academy of Sciences of the United States of America* 97, 538–540). In these cases beryllofluoride acts as a γ-phosphate analog, i.e., high affinity binding of the beryllofluoride analog requires the presence of a nucleoside diphosphate in the catalytic nucleotide site of the enzyme. Furthermore, these analogs tend to decrease or completely inhibit catalytic activity, i.e. ATPase or other activity of the modified enzyme is substantially decreased or undetectable.

There is a need for stable acyl phosphate analogues, particularly apartyl phosphate analogues. The present invention addresses this need.

SUMMARY OF THE INVENTION

The present invention features methods and compositions for production of persistent acyl phosphate analogues (e.g., aspartyl or glutamyl phosphate analogues) using beryllofluoride ($BeF_x$), as well as polypeptides comprising such an acyl phosphate analogue and antibodies that specifically bind to these polypeptides. The invention further features methods of using BeFx analogues in screening assays to identify candidate agent compounds that modulate activity of polypeptides that normally exhibit activity due to the presence of an acyl phosphate linkage (e.g., a phosphorylated aspartate residue as in, e.g., polypeptides involved in signal transduction, polypeptides involved in ion transport across biological membranes, phosphotransferases, etc.). The BeFx polypeptide analogues can also be used to facilitate determination of the structure of the corresponding phosphorylated polypeptide and in rationale drug design.

BRIEF DESCRIPTION OF THE DRAWINGS

(FIG. 1A) The ATPase activity of $NtrC^{WT}$ (FIG. 1B) Formation of open complexes. NtrC was incubated with 100 μM $BeCl_2$ plus 10 mM NaF (filled circles) or 10 mM carbamoyl phosphate (open circles), respectively, at 37° C. for 10 min prior to initiation of the reaction with ATP. (Inset: glnA transcripts) Lanes 1 through 5, $NtrC^{WT}$ (2, 5, 10, 20, 50 nM, respectively).

FIGS. 2A, 2B, and 2C are graphs showing the response of the ATPase activity of NtrC to the concentration of NaF or $BeCl_2$. (FIG. 2A) Dependence of the ATPase activity of $NtrC^{WT}$ (0.4 μM) on the concentration of NaF (0.5 to 200 mM) in the presence of 50 μM $BeCl_2$. (FIG. 2B) Dependence of the ATPase activity of $NtrC^{WT}$ (0.4 μM) on the concentration of $BeCl_2$ (5 to 2,000 μM) in the presence of 5 mM NaF. (FIG. 2C) Response of the ATPase activity of $NtrC^{D86N,S160F}$ (0.2 μM) to the concentration of NaF (5 to 200 mM) in the absence of $BeCi_2$.

(FIG. 12A) The molecules are oriented with the H4-β4-H5 face of CheY directed toward the reader. Some PSP residues that have no structural counterparts in CheY are not shown. (FIG. 12B) A close-up view of the superimposed active sites. This orientation was achieved by applying a −90° rotation along the x-axis to the orientation in (FIG. 12A).

DETAILED DESCRIPTION OF PREFERRED EMBODIMENTS

Figure 1A:
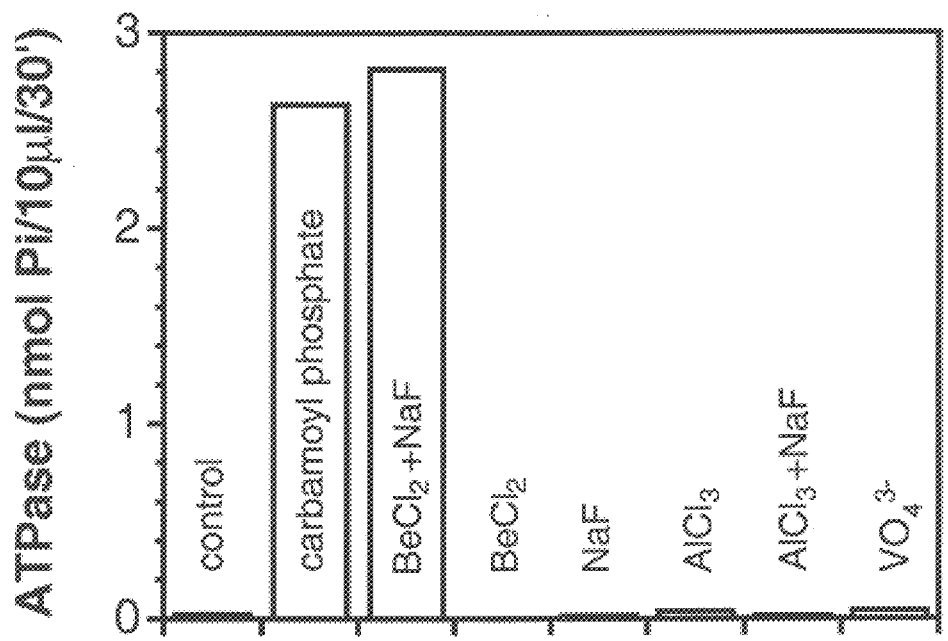
FIGS. 1A and 1B are graphs showing activation of $NtrC^{WT}$ by $BeF_x$.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an analogue" includes a plurality of such analogues, and reference to "the regulator" includes reference to one or more regulators and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "acyl phosphate polypeptide" as used herein is meant to refer to a polypeptide comprising one or more carboxylated amino acids. Of particular interest are polypeptides comprising aspartic acid (aspartate) or glutamic acid (glutamate), either alone or in combination.

"Polypeptide" as used herein refers to an oligopeptide, peptide, or protein, and is meant to encompass polypeptides of any function which are naturally-occurring polypeptides, synthetically produced polypeptides (e.g., synthetic peptides), and recombinantly produced polypeptides, as well as polypeptides comprising a modified amino acid residue (e.g., a non-naturally occurring amino acid residue, etc.) or comprising a chemical modification of the polypeptide backbone structure. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule. Of particular interest are polypeptides which function as response regulators (e.g., NtrC, OmpR, NarL, CheY, SpoOF, DctD, etc.), phosphotransferases, phosphatases (e.g., phosphoserine phosphatase, etc.), phosphomutases, and P-type ATPases. In one embodiment, the P-type ATPases are P-type ATPases other than a CaATPase.

The term "analog" or "analogue" are used interchangeable herein to encompass a polypeptide comprising at least one chemical entity different from the polypeptide from which it is derived (e.g., a polypeptide analog comprising a berryllfluoride group).

The term "functionally active," as used in, for example, the context of "functionally active acyl phosphate polypeptide analog" is meant to indicate that the analog retains activity of a phosphorylated form of the parent polypeptide. For example, a functionally active polypeptide analog is one that exhibits at least about 50%, usually at least about 75%, more usually at least about 80–85% or about 90–95%, or greater of an activity of the unmodified parent polypeptide in its phosphorylated form. Examples of activities include, but are not limited to, activity as a transcriptional regulator, activity as a phosphatase, and the like.

The term "response regulator" as used herein is meant to refer to a polypeptide that participates in the regulation of a response of the cell from which it is derived (e.g., prokaryote (e.g., bacterium) or eukaryote (e.g., mammalian cell)). Of particular interest are response regulators that are naturally activated by phosphorylation of an aspartate residue, e.g. comprise a receiver domain that is phosphorylated at an aspartic acid residue.

The term "receiver domain polypeptide" is meant to refer to a polypeptide of a response regulator polypeptide, which polypeptide minimally encompasses an amino acid residue (e.g., aspartic acid) that is phosphorylated to provide for "activation" of the response regulator. In general, receiver domains control the activity of other domains of the same polypeptide (e.g. the output domain) and/or control activity of other polypeptides. Receiver domains are often involved in regulation of transcription (e.g., by acting as a transcription regulator through DNA binding). Exemplary activities of response regulators include, but are not necessarily limited to DNA binding and ATP hydrolysis.

The term "BeFx analogue" or "BeFx polypeptide analogue" "polypeptide analogue" or "beryllofluoride acyl phosphate analogue" is used herein to encompass an acyl phosphate polypeptide that comprises an acyl phosphate analog comprised of a beryllium atom complexed with fluorine ligands in lieu of a phosphate group at a phosphorylation site.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, preferably 75% free, and most preferably 90% free from other components with which it is naturally associated.

By "binds specifically" is meant high avidity and/or high affinity binding of an antibody to a specific or desired polypeptide(s), e.g., binding to an epitope of a polypeptide of interest, to an epitope of an analog of such a polypeptide, or to an epitope shared by a naturally occurring polypeptide and its analog. Antibody binding to its epitope on this specific polypeptide is preferably stronger than binding of the same antibody to any other epitope, particularly those which may be present in molecules in association with, or in the same sample, as the specific polypeptide of interest. Antibodies that bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to the desired polypeptide or polypeptide analog with a binding affinity of $10^7$ liters/mole or more, preferably $10^8$ l/mole or more, even more preferably $10^9$ l/mole or more, are said to bind specifically. In general, an antibody with a binding affinity of $10^4$ l/mole or less is not useful in that it will not bind an antigen at a detectable level using conventional methodology currently used.

Overview

The invention is based on the surprising discovery that beryllofluoride reacts with a carboxyl group to mimic an acyl phosphate linkage, and further that phospho-aspartate containing polypeptides comprising a BeFx acyl phosphate analogue retain the functional activity of the corresponding phosphorylated native polypeptide. An active beryllofluoride polypeptide analog can be generated from the unphosphorylated, inactive form of the polypeptide to form an active form of the polypeptide that mimics the phosphorylated form of the parent polypeptide. Accordingly, modification of carboxylated amino acids (e.g., aspartic acid (aspartate) or glutamic acid (glutamate), particularly aspartic acid (aspartate)), especially in the context of a polypeptide, is of particular interest. In addition, the beryllofluoride analogs can be formed in the substantial absence of a nucleoside phosphate.

$BeF_x$ forms functionally active acyl phosphate analogues with all response regulators tested to date (a total of six): NtrC, OmpR, NarL, CheY, SpoOF, and DctD, an activator of $\sigma^{54}$-holoenzyme in which the receiver domain acts negatively (Lee et al. (1994) *J. Biol. Chem.* 269, 20401–20409). As assessed by both functional and structural criteria, $BeF_x$ forms an excellent aspartyl phosphate analogue in NtrC, and CheY. Structural studies indicate that $BeF_x$.SpoOF mimics P-SpoOF, and functional studies indicate the same for $BeF_x$-.OmpR and $BeF_x$.NarL. $^1H$-$^{15}N$ HSQC spectra of $BeF_x$ complexes with $NtrC^r$, CheY, and SpoOF were readily obtained and those of $BeF_x$.$NtrC^r$ and $BeF_x$.CheY showed changes in chemical shifts that are characteristic of the corresponding phosphorylated proteins (FIG. 6) (for chemical shifts of the relevant phosphorylated proteins, see, e.g., (Lowry et al. (1994) *J. Biol. Chem.* 269, 26358–26362; Nohaile et al. (1997) *J. Mol. Biol.* 273, 299–316). Determination of the structures of $BeF_x$ complexes with a number of receiver domains will be straightforward; comparison of these structures will facilitate discrimination between general and specific features of the conformational changes that occur upon activation of different receiver domains. Moreover, active $BeF_x$complexes of receiver domains will facilitate study of their interactions with their corresponding output domains, their cognate autokinases/phosphatases, and other components in their signal transduction pathways (Ota and Varshavsky (1993) *Science* 262, 566–569; Maeda et al. (1994) *Nature* (London) 369, 242–245; Ruis and Schüller (1995) *BioEssays* 17, 959–965; Schaller (1997) *Essays Biochem.* 32, 101–111; Perego and Hoch (1996) *Trends Genet.* 12, 97–101).

Figure 7B:
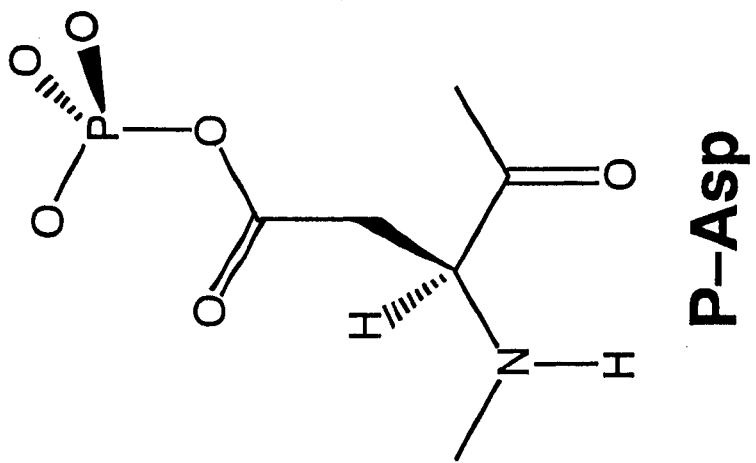
FIGS. 7A and 7B are schematic drawings of the postulated $BeF_3$·aspartate ($BeF_3$·Asp) complex and its biological counterpart, phosphorylated aspartate (P-Asp), in bacterial response regulators. A divalent cation (not indicated) is required for the formation of both species.
Figure 7A:
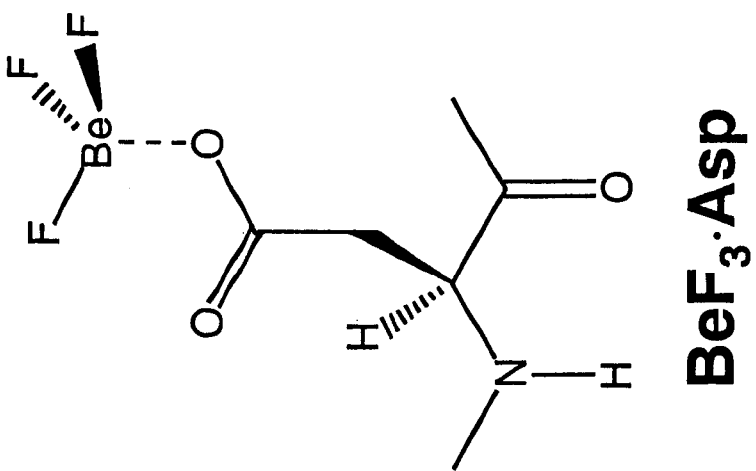

$BeF_x$ forms an acyl phosphate analogue with the active site aspartate of receiver domains (FIGS. 7A and 7B). This is similar to its role in forming the ATP (GTP) analogue $ADP.BeF_x$ ($GDP.BeF_x$) in which it also mimics an acid anhydride linkage (Chabre (1990) *Trends Biochem. Sci.* 15, 6–10). The obligatorily tetrahedral geometry of Be with F and O ligands (Chabre (1990) *Trends Biochem. Sci.* 15, 6–10; Goldstein (1964) *Anal. Chem.* 36, 243–244; Martin (1988) *Biochem. Biophys. Res. Commun.* 155, 1194–1200) suggests that phosphorylated receiver domains are active in their "ground state," rather than in the transition state for hydrolysis of the phosphate, a state that would occur as a consequence of autophosphatase activity or regulated dephosphorylation. In the latter case ligands around the terminal phosphorus would be expected to be planar.

Also of interest are acyl phosphate analogs of polypeptides which function as phosphotransferases, phosphatases, phosphomutases, and P-type ATPases. As assessed by both functional and structural criteria (FIGS. 10–12), $BeF_x$ forms an acyl phosphate analogue with phosphoserine phosphatase (PSP), a member of the HAD superfamily of proteins. HAD family proteins that utilize a phospho-aspartate intermediate have a set of conserved residues that in PSP correspond to Asp 11, Ser 99, Lys 144, Asp 167, and Asp 171. Mutation of any of these residues in human PSP, except Ser to Thr, dramatically decreases the catalytic efficiency. In the active site of $BeF_3^-$.PSP (FIG. 10), these conserved residues come together to form interactions with the aspartyl phosphate analogue ($BeF_3^-$) and/or the catalytically required divalent cation, $Mg^{2+}$. Asp 11Oδ1 is bound to the beryllium (1.5 Å) of $BeF_3^-$. Asp 11-Oδ2, along with a fluorine, Asp 13-C=O, Asp 167-Oδ, and two water molecules occupy the six coordination sites of $Mg^{2+}$. Ser 99-Oγ forms a hydrogen bond with $BeF_3^-$. Lys 144-Nζ forms salt bridges with $BeF_3^-$ and Asp 171-Oδ1. Asp 171-Oδ2 forms hydrogen bonds with the backbone amides of Asp 167 and Gly 168. These two hydrogen bonds appear to stabilize the conformation of the backbone around Asp 167 such that the Asp 167 sidechain is restrained in a position to coordinate with $Mg^{2+}$.

$BeF_x$ analogues are useful in a variety of applications, including, but not limited to, screening assays to identify agents that modulate activity of acyl phosphate polypeptides; generation of specific antibodies that bind to both the beryllofluoride polypeptide analogue and to the naturally phosphorylated acyl phosphate polypeptide; use of antibodies in screening assays and diagnostic assays; and other applications that will be readily apparent to the ordinarily skilled artisan upon reading the disclosure provided herein.

$BeF_x$ analogues lend persistence to an activated polypeptide that, in its natural state, is highly labile and susceptible to inactivation. This feature thus provides persistent analogues of activated polypeptides, as well as methods for screening agents and other uses of these "activated" polypeptides that could not have otherwise been accomplished using the "naturally" activated polypeptide (i.e., the phosphorylated polypeptide). The screening assays provided by the invention will for the first time make it possible to identify and/or design agents that target the activity of acyl phosphate polypeptides, e.g., activated response regulators or polypeptides that act downstream of these regulators, and provide for, for example, new antimicrobial agents. For example, agents that inhibit resistance to the antibiotic vancomycin can be identified by identifying agents that inhibit contact of the appropriate response regulator with its downstream targets.

Specific aspects of the invention will now be described in more detail.

Acyl Phosphate Analogues

Polypeptides comprising a beryllofluoride acyl phosphate analogue are produced by reacting the unphosphorylated acyl phosphate polypeptide with a BeFx phosphate analogue. "BeFx" is used herein to encompass activating species of beryllofluoride of any liganded state, e.g., $BeF_3^-$, $BeF_4^{2-}$. Methods for producing reactive BeFx phosphate analogues are well known in the art, see, e.g., Werber et al. (1992) Biochemistry 31, 7190–7197.

Any of a variety of polypeptides can be combined with a beryllofluoride phosphate analogue to produce the beryllofluoride acyl phosphate polypeptide analogues of the invention. Of particular interest is the production of BeFx analogues of polypeptides that are response regulators, and which effect regulation of, for example, a signal transduction pathway upon phosphorylation. Response regulators of interest can be of prokaryotic or eukaryotic origin, and can be involved in any of a variety of regulated responses such as cell division (Quon et al. (1996) Cell 84, 83–93), development (Fabret et al. (1999) J. Bacteriol. 181, 1975–1983), chemotaxis (Silversmith and Bourret (1999) Trends Microbiol. 7, 16–22), virulence (Dziejman and Mekalanos (1995) in Two-component signal transduction, eds. Hoch and Silhavy, (ASM, Washington, D.C.), pp. 305–317; Haldimann et al. (1997) J. Bacteriol. 179, 5903–5913; Groisman (1998) BioEssays 20, 96–101; Novak et al. (1999) Nature (London) 399, 590–593). Examples of such response regulators include, but are not necessarily limited to NtrC, OmpR, NarL, CheY, SpoOF, and DctD. Other response regulators suitable for modification according to the methods of the present invention will be readily apparent to the ordinarily skilled artisan upon reading the present specification. Response regulators of particular interest are those found in bacteria, yeast, and plants, particularly in bacteria, especially pathogenic bacteria.

Also of particular interest is the production of BeFx analogues of polypeptides that are phosphotransferases, phosphatases, phosphomutases, or P-type ATPases. Each of these polypeptides have functional activities in their phosphorylated forms, or their phosphorylated forms playa key role in their functional activity. For example P-type ATPases play major roles in ion transport across membranes, and thus the production of a stable phosphorylated form can be important in identification of drugs that interact with this polypeptide.

In one embodiment, the invention is used to produce a BeFx polypeptide analogue that minimally comprises an amino acid sequence of a receiver domain of a response regulator. Such receiver domain polypeptide analogues of the invention can be relatively small (e.g., from about 10 amino acid residues to about 300 amino acid residues, generally from about 20 to about 125 amino acid residues). Response regulator polypeptides can vary in size from a polypeptide composed primarily of a receiver domain up to about 1,000 amino acid residues or more.

In another embodiment, the invention is used to produce a BeFx polypeptide analogue that minimally comprises an amino acid sequence of a phosphotransferase, phosphatase, phosphomutase, or P-type ATPase. Such phosphotransferase, phosphatase, phosphomutase, or P-type ATPase polypeptide analogues of the invention can be relatively small (e.g., from about 10 amino acid residues to about 300 amino acid residues, generally from about 20 to about 125 amino acid residues). phosphotransferase, phosphatase, phosphomutase, or P-type ATPase polypeptides can vary in size from a polypeptide composed primarily of a phosphorylation site up to about 1,000 amino acid residues or more.

Antibodies that Bind to Beryllofluoride Acyl Phosphate Analogues and their Corresponding Naturally Occurring Phosphorylated Parent Polypeptides The polypeptide analogues of the invention can be used to generate antibodies that specifically bind not only the polypeptide analogue used to generate the antibodies, but also specifically bind the naturally phosphorylated acyl phosphate polypeptide. Furthermore, the BeFx analogues of invention can be used to generate antibodies that specifically bind the corresponding phosphorylated amino acid residue (e.g., phosphorylated aspartic acid, phosphorylated glutamic acid, and the like). Antibodies that specifically bind to the phosphorylated form of the naturally occurring acyl phosphate polypeptide, or that specifically bind the corresponding phosphorylated amino acid residue, can be used in a variety of applications including, but not limited to, isolation of the phosphorylated polypeptide, qualitative and quantitative assays in detection of phosphorylated polypeptides (e.g., as in diagnostic assays), and the like.

Anti-BeFx polypeptide analogue antibodies of the invention include, but are not limited to, polyclonal, monoclonal, chimeric, single chain, Fab fragments and fragments produced by a Fab expression library. Antibodies of particular interest include, for example, antibodies that inhibit activity of the phosphorylated polypeptide (e.g., to modulate a signal transduction pathway by, for example, modulating DNA binding of the phosphorylated response regulatory polypeptide, modulating interaction of the phosphorylated response regulatory polypeptide with a polypeptide downstream in the regulatory pathway, and the like). Such antibodies may be useful in, for example, modulation of a regulatory pathway, in screening assays for agents that modulate activity of the phosphorylated polypeptide (e.g., DNA binding activity to, for example, promote gene transcription) or activity of a downstream effector polypeptide or other gene product, and in measurement of phosphorylated polypeptides in a sample.

Methods for generating antibodies are well known in the art. In the instant case, methods that are based upon in vitro screening assays are preferred in view of the toxicity of BeFx for the animal hosts normally used to generate antibodies.

Preferably, antibodies are produced by screening recombinant immunoglobulin libraries or panels of highly specific binding reagents as disclosed in Orlandi et al. (1989, Proc Natl Acad Sci 86: 3833–3837), and Winter et al.(1991; Nature 349:293–299). Techniques developed for the production of "chimeric antibodies", the splicing of mouse antibody genes to human antibody genes to obtain a molecule with appropriate antigen specificity and biological activity can be used (Morrison et al. 1984 Proc Natl Acad Sci 81:6851–6855; Neuberger et al. 1984 Nature 312:604–608; Takeda et al. 1985 Nature 314:452–454). Alternatively, techniques described for the production of single chain antibodies (U.S. Pat. No. 4,946,778) can be adapted to produce single chain antibodies.

Antibody fragments having specific binding sites for a BeFx polypeptide analogue can also be generated. For example, such fragments include, but are not limited to, F(ab')2 fragments, which can be produced by pepsin digestion of the antibody molecule, and Fab fragments, which can be generated by reducing the disulfide bridges of the F(ab')2 fragments. Alternatively, Fab expression libraries can be constructed to allow rapid and easy identification of monoclonal Fab fragments with the desired specificity (Huse et al 1989 Science 256:1275–1281).

A variety of protocols for competitive binding or immunoradiometric assays using either polyclonal or monoclonal antibodies having established antigen specificities are well known in the art. Such immunoassays typically involve, for example, the formation of complexes between a BeFx polypeptide analogue of the invention (or the phosphorylated polypeptide to which the BeFx analogue corresponds) and a specific antibody, and the detection and quantitation of antigen-antibody complex formation. A two-site, monoclonal-based immunoassay utilizing monoclonal antibodies reactive to two noninterfering epitopes on a specific response regulator polypeptide is preferred, but a competitive binding assay can also be employed. These assays are described in Maddox et al 1983, J Exp Med 158:1211.

Screening Methods

The BeFx polypeptide analogues of the invention can be used to identify compounds that affect the activity of the phosphorylated form of the corresponding naturally-occurring acyl phosphate polypeptide by, for example, specifically binding the phosphorylated polypeptide and affecting its function or by modulating the activity of an upstream or downstream effector molecule. Identification of such compounds can be accomplished using any of a variety of drug screening techniques. Of particular interest is the identification of agents that have activity in affecting function of response regulators, phosphotransferases, phosphatases, phosphomutases, or P-type ATPases. Such agents are candidates for, for example, development of new therapeutic compounds and methods of treatment using same. For example, where the corresponding phosphorylated polypeptide is a regulatory microbial polypeptide, the screening methods of the invention can be used to identify new antimicrobial compounds useful in prevention or treatment of microbial infection (e.g., provide for antibacterial or bacteriostatic compounds in treatment of infection by a pathogenic bacterium in a subject). Of particular interest are screening assays for agents that have a low toxicity for human cells and, where appropriate, increased specificity for the target pathogen (e.g., bacteria, yeast, parasite, etc.).

The BeFx polypeptide analogue employed in such a test can be free in solution, affixed to a solid support, or present on a cell surface. The screening assays of the invention are generally based upon the ability of the agent to bind to a BeFx polypeptide analogue (e.g., to provide for modulation of activity by, for example, steric hindrance), bind to an upstream or downstream effector molecule that interacts with the corresponding naturally phosphorylated polypeptide, and/or elicit or inhibit a biological activity associated with the corresponding naturally occurring phosphorylated polypeptide (i.e., a functional assay or an assay using radioligand binding assays). In short, any assay that one might wish to perform with the naturally occurring phosphorylated response regulator polypeptide, phosphotransferase, phosphatase, phosphomutase, or P-type ATPase can be performed with the corresponding BeFx polypeptide analogue of the invention. The BeFx polypeptide analogue provides that advantages of persistence of the activated form of the polypeptide, an increased, consistent level of activated response regulator polypeptide, phosphotransferase, phosphatase, phosphomutase, or P-type ATPase, and the ability to run assays and other studies under relatively unchanging conditions (e.g. with a relatively constant amount of an activated form of the acyl phosphate polypeptide) for a relatively long period of time (e.g., hours to days).

The term "agent" as used herein describes any molecule, e.g. protein or pharmaceutical, with the capability of altering (i.e., eliciting or inhibiting) or mimicking a desired physiological function of the naturally phosphorylated acyl phosphate polypeptide that corresponds to the BeFx polypeptide analogue of the invention. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts (including extracts from human tissue to identify endogenous factors affecting response regulator polypeptide activity) are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Preferably, the drug screening technique used provides for high throughput screening of compounds having suitable binding affinity to BeFx polypeptide analogue and/or eliciting a desired response normally associated with the corresponding naturally occurring acyl phosphate polypeptide. For example, large numbers of different small peptide test compounds can be synthesized on a solid substrate, such as plastic pins or some other surface (see, e.g., Geysen WO 84/03564, published on Sep. 13, 1984), the peptide test compounds contacted with polypeptide analogues, unreacted materials washed away, and bound polypeptide analogues detected by virtue of a detectable label or detection of a biological activity associated with the polypeptide analogue. Purified BeFx polypeptide analogue can also be coated directly onto plates for use in such in vitro drug screening techniques. Alternatively, non-neutralizing antibodies can be used to capture the polypeptide analogue and immobilize it on a solid support.

The invention also contemplates the use of competitive drug screening assays in which BeFx polypeptide neutralizing antibodies compete with a test compound for binding to the downstream target (e.g., effector polypeptide or effector molecule with which the native phosphorylated polypeptide interacts).

Screening of Candidate Agents

A wide variety of assays may be used for identification of agents of interest, including labeled in vitro binding assays, immunoassays for protein binding, and the like. For example, by providing for the production of large amounts of persistent BeFx polypeptide analogues, one can identify ligands or substrates that bind to, modulate or mimic the action of these proteins. The purified BeFx polypeptide analogue can also be used for determination of three-dimensional crystal or NMR structure of the isolated BeFx polypeptide analogue or complexes of BeFx polypeptide analogue with its target (e.g., bound to DNA or bound to an effector molecule, e.g., effector polypeptide). The three-dimensional structure can be used for modeling intermolecular interactions of the corresponding naturally occurring phosphorylated acyl phosphate polypeptide, and can serve as the basis for rationale drug design (e.g., design of molecules that reversibly or irreversibly bind to the active, phosphorylated form of the corresponding native polypeptide to inhibit or otherwise modulate the polypeptide's activity, that mimic the three-dimensional structure of the active, phosphorylated form of the corresponding native polypeptide to reversibly or irreversibly bind the downstream target of the polypeptide (e.g., to bind an effector polypeptide) to disrupt or otherwise modulate the pathway in which the polypeptide is involved. Methods for performing such structural determinations upon an isolated polypeptide are well known in the art.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g. albumin, detergents, etc that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 24 hours, usually on the order of from about 30 min to 1 hour will be sufficient. In general, the longer the overall time required by the assay, the more advantageous is the use of the BeFx analogues of the invention since BeFx analogues are far more persistent than the corresponding naturally occurring phosphorylated acyl phosphate polypeptide.

Functional Screening Assays

Candidate agents can be screened for agonistic or antagonist action in modulating BeFx polypeptide analogues activity in a functional assay, e.g., an assay that monitors a biological activity associated with the corresponding naturally occurring phosphorylated acyl phosphate polypeptide such as DNA binding, ATP hydrolysis, etc. The functional assay can be based upon detection of a biological activity of a BeFx polypeptide analogue that can be assayed using high-throughput screening of multiple samples simultaneously, e.g., a functional assay based upon ATPase activity. Such functional assays can be used to screen candidate agents for activity as either agonists or antagonists.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following procedures are used in the Examples described in detail below. Although some of the methods described below are in common use, the specific protocol used in the Examples below is described in detail where alternative protocols are often employed. Basic procedures are not described, as such are well within the skill of the ordinarily skilled artisan and, in some instances, are carried out with a kit and/or according to the reagent manufacturer's instructions.

Phosphate analogs. $BeF_x$ and $AlF_x$ were generated in situ with NaF in the mM range and $BeCl_2$ or $AlCl_3$ in the $\mu$M range (Lunardi et al. (1988) *Proc. Natl. Acad. Sci. USA* 85, 8958–8962; Werber et al. (1992) *Biochemistry* 31, 7190–7197). $VO_4^{3-}$ was prepared as described previously and used in the mM range (Goodno (1979) *Proc. Natl. Acad. Sci. USA* 76, 2620–2624). Phosphate analogues had been formed correctly as evidenced by the ability of all of the above compounds to inhibit the ATPase activity of myosin subfragment 1 (Sigma) in the presence of ADP.

NtrC proteins. $NtrC^{D86N,S160F}$ combines two constitutive amino acid substitutions and is our most active constitutive NtrC protein; i.e., it has the highest activity in the absence of phosphorylation (Flashner et al. (1995) *J. Mol. Biol.* 249, 700–713). Phosphorylation further increases its activity. All full-length NtrC proteins (dimer concentration) were maltose binding protein fusions to NtrC lacking its two natural cysteines (MBP-$NtrC^{C30V,C364A}$) or its derivatives. MBP-$NtrC^{C30V,C364A}$ has been shown to be as active as native NtrC protein (Klose et al. (1994) *J. Mol. Biol.* 241, 233–245; Hwang et al. (1999) *Proc. Natl. Acad. Sci. USA* 96, 4880–4885).

Assays. The ATPase activity of $NtrC^{WT}$ (1 $\mu$M) was assayed in HEPES buffer, pH 7.3, by monitoring the release of $P_i$ from $\gamma^{32}P$-ATP at 25° C. for 30 min as described (Flashner et al. (1995) *J. Mol. Biol.* 249, 700–713). Prior to addition of ATP, other components were incubated for 30 min at 25° C. together with the indicated small molecule or combination of small molecules (carbamoyl phosphate, 10 mM; $BeCl_2$, 200 $\mu$M; $AlCl_3$, 200 $\mu$M; NaF, 5 mM; $VO_4^{3-}$, 1 mM). The response of the ATPase activity of NtrC to the concentration of NaF or $BeCl_2$ was assessed essentially as above, except the reaction time was 10 min.

Formation of open complexes was assessed in a single-cycle transcription assay on a supercoiled plasmid template pJES534 (1 nM) (Porter et al. (1993) *Genes Dev.* 7, 2258–2273; Flashner et al. (1995) *J. Mol. Biol.* 249, 700–713). NtrC was incubated with 100 μM $BeCl_2$ plus 10 mM NaF or 10 mM carbamoyl phosphate, respectively, at 37° C. for 10 min prior to initiation of the reaction with ATP.

Fe-mediated cleavage of NtrC was assessed as follows: NtrC (5 to 10 μM) was incubated for 30 min at 25° C. with the indicated small molecule or combination of small molecules (carbamoyl phosphate, 10 mM; $BeCl_2$, 200 μM; NaF, 10 mM) in cleavage buffer (10 mM MOPS, pH 8.0, 50 mM KCl, 8 mM $MgCl_2$, 5% glycerol, 1 mM EDTA). Then cleavage was initiated by adding $H_2O_2$ and sodium ascorbate to final concentrations of 50 mM and samples were subjected to analysis by SDS-PAGE as described (Greiner etal. (1997) *Bioconjugate Chem.* 8, 44–48).

Figure 4:
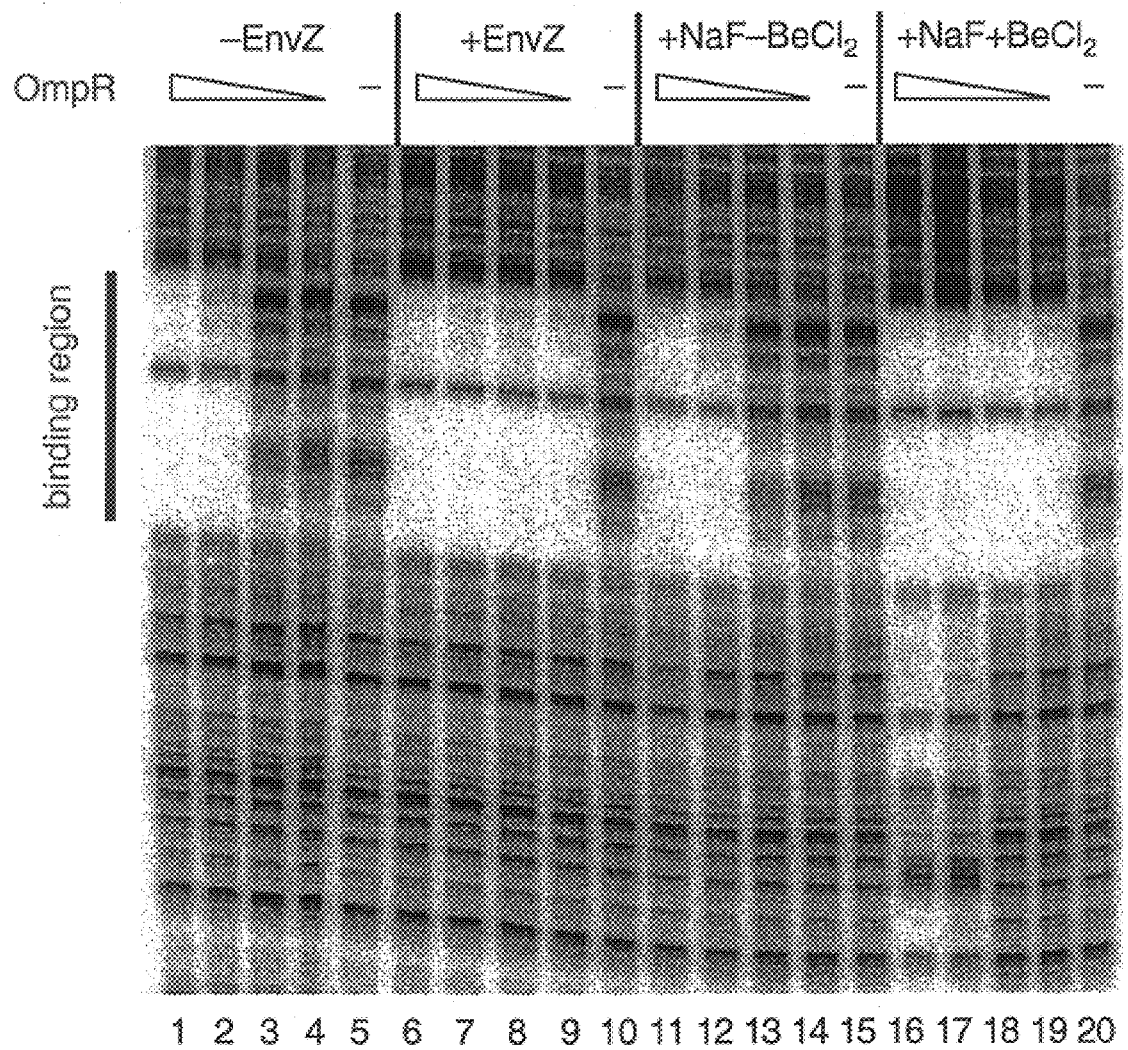
FIG. 4 is a photograph showing $BeF_x$ stimulation of the binding of OmpR to the ompF promoter-regulatory region. The concentrations of OmpR were: 6.4 μM (lanes 1, 6, 11 and 16); 1.6 μM (lanes 2, 7, 12 and 17); 0.4 μM (lanes 3, 8, 13 and 18); 0.1 μM (lanes, 4, 9, 14 and 19); and 0 μM (lanes 5, 10, 15 and 20). For samples in lanes 6–10, OmpR was phosphorylated by MBP-EnvZ (0.3 μM). For samples in lanes 11–20, NaF (10 mM) was present and for those in lanes 16–20, $BeCl_2$ (100 μM) was also present.

Binding of $BeF_x$.OmpR to the ompF promoter-regulatory region was assessed by DNase I footprinting as described in Huang and Igo (1996) *J. Mol. Biol.* 262, 615–628 and was compared to that of P-OmpR. The concentrations of OmpR were: 6.4 μM (lanes 1, 6, 11 and 16); 1.6 μM (lanes 2, 7, 12 and 17); 0.4 μM (lanes 3, 8, 13 and 18); 0.1 μM (lanes, 4, 9, 14 and 19); and 0 μM (lanes 5, 10, 15 and 20). For samples in lanes 6–10, OmpR was phosphorylated by MBP-EnvZ (0.3 μM) as described (Huang and Igo (1996) *J. Mol. Biol.* 262, 615–628). For samples in lanes 11–20, NaF (10 mM) was present and for those in lanes 16–20, $BeCl_2$ (100 μM) was also present. Non-specific DNA-binding observed in the presence of $BeCl_2$ and NaF in lanes 16 and 17 was not observed when OmpR was phosphorylated by EnvZ (lanes 6 and 7) unless much higher concentrations of OmpR were used (see FIG. 4).

FliM peptide binding of CheY was assessed as described in McEvoy et al. (1999) *J. Mol. Biol.* 289, 1423–1433. Fluorescence intensity of CheY (10 μM) at 340 nm was measured as a function of added FliM peptide in the absence or presence of 2 mM $BeCl_2$, 20 mM NaF and 20 mM $MgCl_2$.

Transcriptional activation of NtrC was assessed as described in Flashner et al. (1995) *J. Mol. Biol.* 249, 700–713. DNA-binding of OmpR was assessed as described in Huang and Igo (1996) *J. Mol. Biol.* 262, 615–628. DNA-binding of NarL was assessed as described in Li et al. (1994) *J. Mol. Biol.* 241, 150–165 and Darwin et al. (1997) *Mol. Microbiol* 25, 583–595.

NMR chemical shift. $NtrC^r$, CheY, and SpoOF were expressed from plasmid vectors in *Escherichia coli* strain BL21 (DE3) and were purified by a combination of ion exchange chromatography and HPLC. Mass spectroscopy verified that each had the correct molecular mass and was >95% pure. For isotope labeling, cells were grown in minimal medium (M9) supplemented with trace metals and biotin and containing labeled $^{13}C$ glucose and/or $^{15}N$ ammonium chloride (2 g/l). NMR assignments were obtained using HSQC, HNCA, and $^{15}N$ resolved NOESY for $NtrC^r$, and HSQC, HNCACB, HNCA, CBCACONH, and $^{15}N$ NOESY for CheY.

Figure 9A:
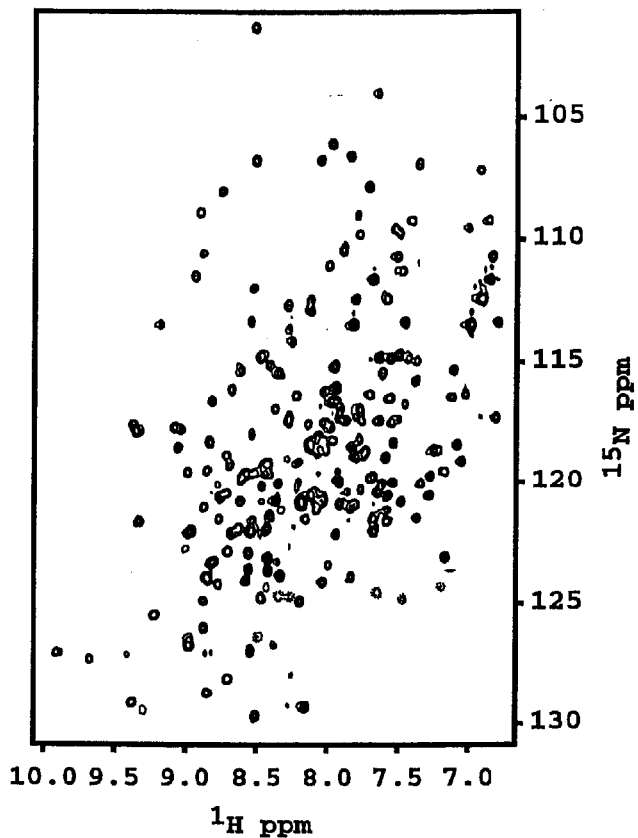
FIGS. 9A and 9B depict the $^1H$-$^{15}N$ FHSQC spectra of PSP before (A) and after (B) $BeF_3^-$ complexation (A) 0.5 mM PSP and 5 mM $MgCl_2$. (B) 0.5 mM PSP, 5 mM $MgCl_2$, 3 mM NaF and 0.6 mM $BeCl_2$. The crosses in (B) represent the crosspeak positions in (A). Both spectra were recorded at 308 K and pH 6.5.
Figure 9B:
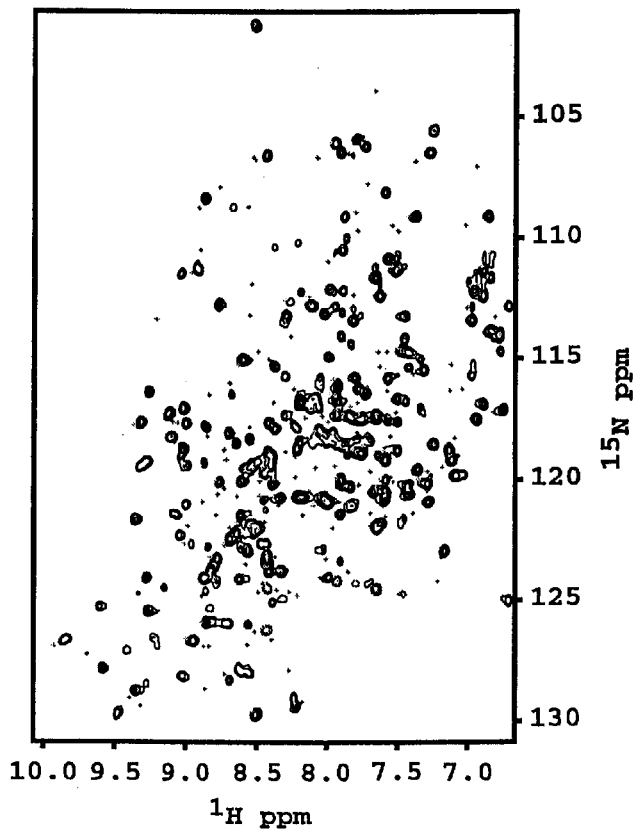

PSP from *Methanococcus jannaschii* was cloned, expressed and purified using methods described previously. Uniformly $^{15}N$ labeled protein samples for NMR spectroscopy were prepared by growth in M9 minimal medium with $^{15}N$ ammonium chloride as the sole nitrogen source. $^1H$-$^{15}N$ FHSQC spectra were collected on an AMX 600 NMR spectrometer. Sample conditions are described in the FIG. 9 legend.

Crystallization. PSP was concentrated to 54 mg/ml in a buffer containing 20 mM Tris-HCl, pH 7.5, 0.3 M NaCl, 1 mM EDTA, and 10 mM DTT. Crystals wre grown using the hanging drop vapor diffusion method with seeding. Concentrated NaF, $BeCl_2$, and $MgCl_2$ were added to the protein sample to reach final concentrations of 54 mM, 10.8 mM, and 90 mM, respectively, while keeping the protein concentration effectively unchanged. One μL of this sample was then mixed with 1 μL of the well solution containing 0.1 M sodium acetate buffer at pH 4.5, 0.5 M sodium phosphate dihydrate, and 22% polyethylene glycol 2000 monomethylether (PEG2K MME). Micro-seeding was performed 1 hour after the drop was set up. Crystals appeared within 12 hours and reached a maximum size of 0.3×0.5×0.5 $mm^3$. The concentration of PEG2K MME was then raised to 30% in order to stabilize the crystals.

Data Collection and Structure Refinement. A crystal from the crystallization drop was used directly for cryo-crystallography data collection. X-ray diffraction data were collected at the Advanced Light Source (ALS) beam line 5.0.2 using an Area Detector System Co. (ADSC) Quantum 4 CCD detector placed 130 mm from the crystal. The data were processed using the programs DENZO and SCALEPACK (Otwinowski, Z., et al., (1996) *Methods in Enzymology* 276, 307–326). X-ray data statistics are shown in Table 1a.

The protein part of a previously determined PSP structure was used for initial rigid-body refinement to obtain a preliminary model. An electron density map calculated from this model clearly showed densities consistent with the fluorine atoms of a $BeF_3^-$ that is bound to Asp 11 with a beryllium-oxygen bond distance of 1.55 Å. This density was used to build the beryllofluoride aspartate residue into the model that was further refined against data up to 1.5 Å using the programs CNS (Brtinger et al. (1998) *Acta Crystallographica. Section D: Biological Crystallography* 54, 905–921) and O (Jones et al. (1991) *Acta Crystallographica. Section A, Crystal Physics, Diffraction, Theoretical and General Crystallography* 47, 110–119). The NCS constraints and restraints were completely released during the refinement. Ten percent of the data were randomly picked out for free R factor cross validation. The refinement statistics are shown in Table 1b.

TABLE 1a

Statistics of X-ray diffraction data and structure refinement.

| Data set | Edge |
|---|---|
| Wavelength | 0.9686 Å |
| Resolution | 30.0–1.5 Å |
| Redundancy | 4.3 (2.75) |
| Unique reflections | 67186 (3066) |
| Completeness of data (%) | 93.8 (86.5) |
| I/σ | 15.9 (3.3) |
| $Rsym^b$ (%) | 6.7 (24.8) |

[a]Numbers in ( )'s are related to the highest resolution shell, which is 1.53–1.50 Å
[b]$R_{sym} = \Sigma_{hkl} \Sigma_i |I_{hkl,i} - <I>_{hkl}| / \Sigma | <I>_{hkl} |$ TABLE 1b Crystal parameters and refinement statistics.

| | |
|---|---|
| Space group | $P2_12_12$ |
| Cell dimensions | a = 68.8 b = 69.8Å c = 91.6Å |
| Volume fraction of protein | 53% |
| $V_m$ ($Å^3$/Dalton) | 2.33 |
| Total number residues | 419 |
| Total non-H atoms | 3709 |
| Number of water molecules | 402 |

TABLE 1b-continued

Crystal parameters and refinement statistics.

| | |
|---|---|
| Number of phosphate molecules | 2 |
| Number of Mg$^{2+}$ | 2 |
| Temperature factors | |
| Protein | 14.2 Å$^2$ |
| Solvent | 23.2 Å$^2$ |
| Metal | 8.9 Å$^2$ |
| phosphate | 13.1 Å$^2$ |
| Resolution range of reflections used | 20–1.5 Å |
| Amplitude cutoff | No |
| R factor | 19.0% |
| Free R factor | 21.1% |
| Stereochemical ideality: | |
| bond | 0.014 Å |
| angle | 1.80° |
| improper | 1.25° |

Example 1

Functional Evidence that BeF$_x$ Activates NtrC

In the process of determining whether well-studied ATP analogs (Goodno( 1979) i Proc. Natl. Acad. Sci. USA 76, 2620–2624; Chabre (1990)*Trends Biochem. Sci.* 15, 6–10; Wittinghofer (1997) *Curr. Biol.* 7, R682–R685) could inhibit the ATPase activity of *S. typhimurium* NtrC, the effects of the analogs were tested on a constitutive mutant form of NtrC, a form that has the capacity to hydrolyze ATP and activate transcription without being phosphorylate (Magasanik (1996) in *Regulation of gene expression in Escherichia coli*, eds. Lin & Lynch (R. G. Landes Co., Austin), pp. 281–290; Rombel et al. (1998) *Cold Spring Harbor Symp. Quant. Biol.* 63, 157–166; Porter et al. (1995) in *Two-component signal transduction*, eds. Hoch and Silhavy (ASM, Washington, D.C.), pp. 147–158; Flashner et al. (1995) *J. Mol. Biol.* 249, 700–713). In contrast to the case for many other purine nucleotide-binding proteins with a mononucleotide fold (Lunardi et al. (1988) *Proc. Natl. Acad. Sci. USA* 85, 8958–8962; Werber et al. (1992) *Biochemistry* 31, 7190–7197; Goodno (1979) *Proc. Natl. Sci. USA* 76, 2620–2624; Chabre (1990) *Trends Biochem. Sci.* 15, 6–10; Wittinghofer (1997) *Curr. Biol.* 7, R682–R685), neither ADP.BeF$_x$ nor ADP.AlF$_x$ nor ADP.VO$_4^{3-}$ appeared to inhibit the ATPase activity of NtrC$^{D86N,S160F}$. Strikingly, BeF$_x$, but not Alf$_x$ (aluminofluoride) or VO$_4^{3-}$ (orthovanadate), substantially stimulated the ATPase activity of unphosphorylate NtrC$^{D86N,S160F}$. This led us to postulate that BeF$_x$ might be forming an acyl phosphate analouge in the receiver or regulatory domain of NtrC$^{D86N,S160F}$, which sould stimulate its constitutive ATPase activity.

Figure 1B:
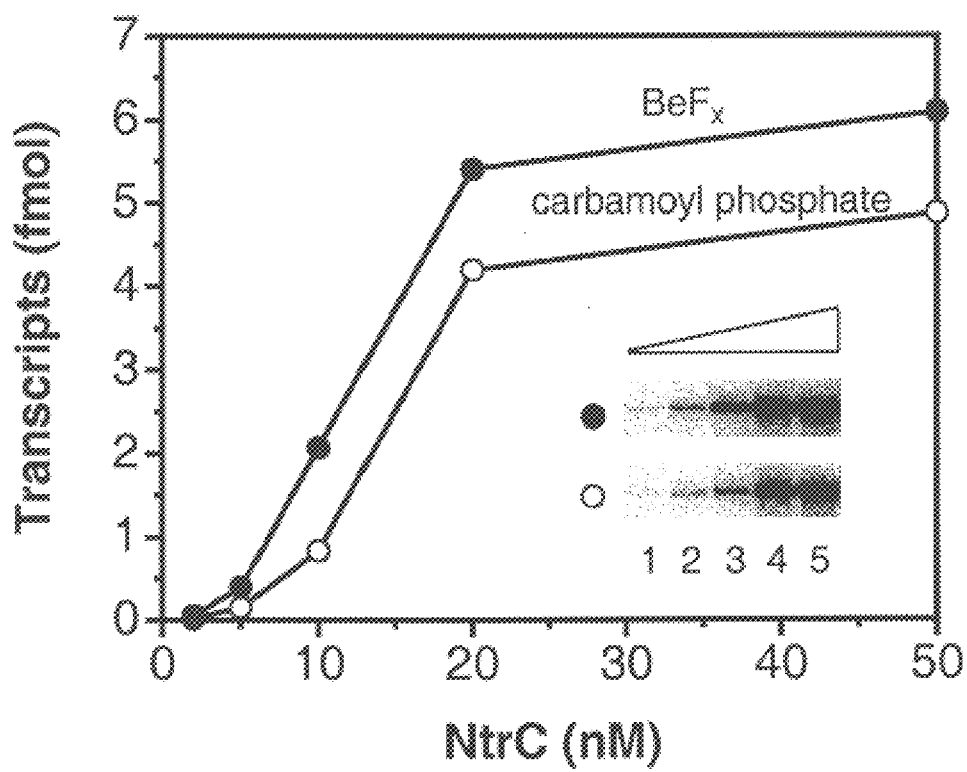

The capacity of BeF$_x$ to substitute for phosphorylation of NtrC was assessed by comparing the effects of BeF$_x$ on wild-type NtrC (NtrC$^{WT}$) to those of the low molecular weight phosphodonor carbamoyl phosphate (Lukat et al. (1992) *Proc. Natl. Acad. Sci. USA* 89,718–722; Feng et al. (1992) *J. Bacteriol.* 174, 6061–6070). Receive domain autophosphorylate from low molecular weight phosphodonors such as carbamoyl phosphate, acetyl phosphate or phosphoramide (Lukat et al. ((1992) *Proc. Nat. Acad. Sci. USA* 89, 718–722; Feng et al. (1992) *J. Bacteriol.* 174, 6061–6070) and also catalyze their own dephosphorylation (Parkinson and Kofoid (1992) *Annu. Rev. Genet.* 26, 71–112; Stock et al. (1995)in *Two-component signal transduction* eds. Hoch and Silhavy (ASM, Washington, D.C.), pp. 25–51). BeF$_x$, which is formed in situ from BeCl$_2$ and NaF (Goldstei (1964) *Anal. Chem.* 36, 243–244; Martin (1988) *Biochem. Biophys. Res. Commun.* 155, 1194–1200), was as effective as carbamoyl phosphate in stimulating the AtPase activity of NtrC$^{WT}$ (FIG. 1A). Both BeCl$_2$ and NaF were required and neither AlF$_x$ nor VO$_4^{3-}$ could substitute. Further BeF$_x$ allowed NtrC$^{WT}$ to activate transcription by $\sigma^{54}$-holoenzyme, its ultimate biological output (FIG. 1B). Impressively, the activity of NtrC$^{WT}$ in the presence of $\leq 100$ $\mu$M BeF$_x$ was at least as great as that of the phosphorylated protein (P-NtrC$^{WT}$) in the presence of 10 mM carbamoyl phosphate. It was shown previously that carbamoyl phosphate yields in vitro activities of NtrC$^{WT}$ comparable to those observed when the protein is phosphorylated by its cognate protein phosphodonor, the histidien autokinase NtrB (Feng et al. (1992) *J. Bacteriol.* 174, 6061–6070)

Example 2

Characterization of BeF$_x$ and its Interaction with NtrC

In order to determine a probable number for x in the activating species BeF$_x$, the effects different concentrations of NaF on the ATPase activity of NtrC$^{WT}$ were tested in the presence of a fixed concentration of BeCl$_2$(50 $\mu$M) (Goldstein (1964) *Anal. Chem.* 36, 243–244; Martin (1988) *Biochem. Biophys. Res. Commun.* 155, 1194–1200). Depending on the excess of F$^-$, different species of BeF$_x$ usually predominate in aqueous solution. No ATPase activity was observed for NtrC$^{WT}$ until the concentration of NAF reaches 1 mM (FIG. 2A), and maximum activity was reached between 5 and 20 mM NaF. Based on previous evidence (Goldstein (1964) *Anal. Chem.* 36, 243–244; Martin (1988) *Biochem. Biophys. Res. Commun.* 155, 1194–1200), (H$_2$O)BeF$_3^-$ is likely to be the species that yields the active form of NtrC. However, for both theoretical and technical reasons (see below), we cannot exclude BeF$_4^{2-}$ as an activating species. Whatever the activating species of BeF$_x$, we postulate that it is likely to form an acyl phosphate analog of NtrC with a bond to an oxygen of the β-carboxyl group of D54. That regulatory effects of BeF$_x$ are exerted through D54, as are those of phosphorylation, is indicated by the failure of BeF$_x$ to stimulate the ATPase activity of mutant forms of NtrC in which D54 has been replaced by A or N (data not shown).

To assess the affinity of NtrC$^{WT}$ for BeF$_x$, we determined the ATPase activity of the protein at a fixed concentration of NaF (5 mM), at which the most abundant species of BeF$_x$ is probably (H$_2$O)BeF$_3^-$ (Goldstein (1964) *Anal. Chem.* 36, 243–244; Martin (1988) *Biochem. Biophys. Res. Commun.* 155, 1194–1200), and different concentrations of BeCl$_2$ (FIG. 2B). ATPase activity was detected even at 5 $\mu$M BeCl$_2$, the lowest concentration tested, which was only about 6-fold higher than the concentration of NtrC (0.8 $\mu$M monomer). The highest ATPase activity was achieved at 100 $\mu$M BeCl$_2$. In both the dose response curves to BeCl$_2$ (FIG. 2B) and NaF (FIG. 2A), inhibition of the ATPase activity of NtrC occurred at high concentrations ($\geq 200$ $\mu$M BeCl$_2$ or $\geq 50$ mM NaF). Additional experiments indicated that either trace amounts of BeCl$_2$ alone or high concentrations of NaF (FIG. 2C) inhibited the ATPase activity of the constitutive form NtrC$^{D86N,S160F}$. Inhibitory effects of high concentrations of NaF on the ATPase activity of NtrC precluded our determining whether BeF$_4^{2-}$ might be an activating species (see above).

Example 3

Structural Evidence that BeF$_x$ Activates NtrC

Figures 3A, 3B:
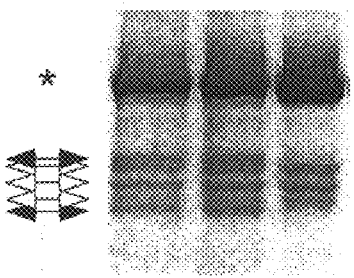
FIGS. 3A and 3B are photographs showing Fe-mediated cleavage of $NtrC^{D86C,Fe}$. Lane 1, molecular weight markers; Lane 2, $NtrC^{D86C}$; Lanes 3 through 7 and 1' through 3', $NtrC^{D86C}$ derivatized with the cysteine-specific Fe chelate (1-[p-(bromoacetamido)benzyl]-EDTA-Fe). The sample in lane 2' contained the same components as that in lane 5. $MgCl_2$ was eliminated from the sample in lane 3' and was replaced with 8 mM $MnCl_2$ in the sample of lane 1'. *, full length NtrC; filled arrows, phosphorylation-dependent cleavage bands (two); unfilled arrows, phosphorylation-independent cleavage bands. (Although there are four bands total, produced from two independent cleavages, only three bands are visible on this gel.)

We have two direct lines of evidence that BeF$_x$ mimics effects of phosphorylation of NtrC structurally as well as functionally. First, $BeF_x$ yields an otherwise phosphorylation-dependent cleavage of $NtrC^{D86C}$ that has been derivatized with an iron chelate ($NtrC^{D86C,Fe}$) (FIG. 3) (Greiner, D. P., Miyake, R., Moran, J. K., Jones, A. D., Negishi, T., Ishihama, A., & Meares, C. F. (1997) *Bioconjugate Chem.* 8, 44–48 (Greiner et al. (1997) *Bioconjugate Chem.* 8, 44–48). This cleavage, which occurs outside the N-terminal receiver domain of NtrC, is indicative of a conformational change in the protein upon activation that allows the N-terminal domain of one monomer to contact the central or output domain of the opposite monomer in a dimer. Rearrangement at the dimer interface of P-NtrC is postulated to drive the formation of active oligomers. Unlike the ATPase activity of NtrC or its capacity to activate transcription, Fe-mediated protein cleavage is not dependent upon a divalent cation (Greiner et al. (1997) *Bioconjugate Chem.* 8, 44–48), and the two phosphorylation- and $BeF_x$-independent cleavages that occur within the receiver domain of NtrC did not require one. By contrast, the $BeF_x$-dependent cleavage did require a divalent cation, and either $Mg^{2+}$ or $Mn^{2+}$ could serve (FIG. 3B). Thus, like phosphorylation (Parkinson and Kofoid (1992) *Annu. Rev. Genet.* 26, 71–112; Stock et al. (1995) in *Two-component signal transduction*, eds. Hoch and Silhavy (ASM, Washington, D.C.), pp. 25–51; Lukat et al. (1992) *Proc. Natl. Acad. Sci. USA* 89, 718–722; Feng et al. (1992) *J. Bacteriol.* 174, 6061–6070), the interaction between $BeF_x$ and D54 of NtrC requires a divalent cation. The second line of evidence that the complex between $BeF_x$ and NtrC ($BeF_x$.NtrC) mimics P-NtrC structurally is provided by NMR spectroscopic studies of $BeF_x$ complexed with $NtrC^r$ (see below).

Example 4

Evidence that $BeF_x$ Activates Other Response Regulators/Receiver Domains

To determine whether effects of $BeF_x$ on NtrC could be generalized to other response regulators/receiver domains, we studied four additional proteins: *E. coli* OmpR and NarL, which activate and repress transcription by $\sigma^{70}$-holoenzyme; *E. coli* CheY, which is a central regulator of the chemotactic response; and *Bacillus subtilis* Spo0F, which is part of the phosphorelay controlling initiation of sporulation. OmpR and NarL are two-domain response regulators. OmpR controls expression of outer membrane porin proteins in response to osmolarity and a variety of other signals that are poorly defined (Pratt et al. (1996) *Mol. Microbiol.* 20, 911–917; Egger et al. (1997) *Genes To Cells* 2, 167–184), whereas NarL controls gene expression in response to availability of the respiratory oxidants nitrate and nitrite (Stewart and Rabin (1995) in *Two component signal transduction*, eds. Hoch and Silhavy (ASM, Washington, D.C., USA), pp. 233–252). Although phosphorylation of OmpR affects its DNA-binding activity (Aiba et al. (1989) *J. Biochem.* 106, 5–7), it is not clear whether the N-terminal domain of OmpR acts positively or negatively. However, unlike the case for NtrC, the N-terminal receiver domain of NarL apparently acts negatively: structural studies provide evidence that the unphosphorylated receiver domain of NarL blocks DNA-binding by its C-terminal domain (Baikalov et al. (1996) *Biochemistry* 35, 11053–11061; Baikalov et al. (1998) *Biochemistry* 37, 3665–3676). Protections from cleavage by DNase I indicated that $BeF_x$.OmpR bound to the regulatory region immediately upstream of the ompF promoter better than P-OmpR, whether phosphorylation was achieved with EnvZ (FIG. 4) or with acetyl phosphate (data not shown). Protections from DNase I cleavage and enhancements of cleavage indicated that $BeF_x$.NarL and P-NarL bound similarly to the control region for the fdnG operon (data not shown), but under conditions optimal for the activation of NtrC (200 µM $BeCl_2$, 10 mM NaF and 5 mM $MgCl_2$), $BeF_x$.NarL was less active.

Figure 5:
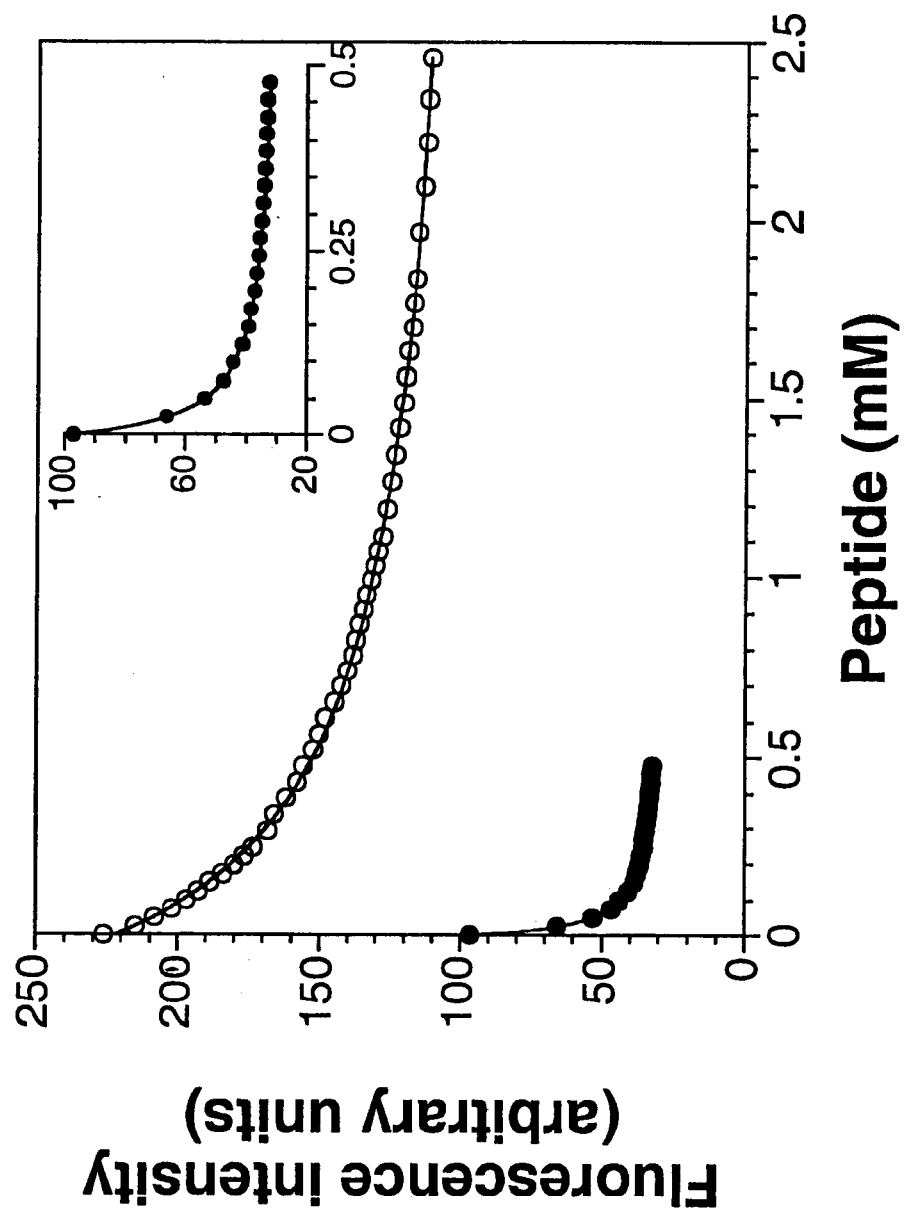
FIG. 5 is a graph showing $BeF_x$ stimulation of the binding of CheY to a FliM peptide (residues 1–16). Fluorescence intensity of CheY (10 μM) at 340 nm as a function of added FliM peptide in the absence (open circles) or presence (closed circles and inset) of 2 mM $BeCl_2$, 20 mM NaF and 20 mM $MgCl_2$.

There is no direct in vitro assay for the activity of P-CheY in reversing the direction of flagellar rotation. Hence, we monitored the effects of BeFx on CheY by measuring its binding to a peptide from FliM (McEvoy et al. (1999) *J. Mol. Biol.* 289, 1423–1433), a component of the switch that controls the direction of flagellar rotation. The strength of this binding, which was assessed by quenching of the intrinsic tryptophan fluorescence of CheY, was recently reported to be phosphorylation-dependent (McEvoy et al. (1999) *J. Mol. Biol.* 289, 1423–1433). The dissociation constants for binding of $BeF_x$.CheY and inactive CheY to the FliM peptide, 26 and 500 µM, respectively (FIG. 5), were the same as those reported for P-CheY and CheY. By this criterion, $BeF_x$.CheY is as active as P-CheY. Like $BeF_x$.CheY, a phosphonate derivative of $CheY^{D57C}$ appears to be a biochemical analogue of P-CheY, but it is difficult to prepare (Halkides et al. (1998) *Biochemistry* 37, 13674–13680). Such analogues are extremely useful because the acyl phosphate linkage of P-CheY is exceptionally labile (half life of seconds) (Parkinson and Kofoid (1992) *Annu. Rev. Genet.* 26, 71–112; Stock et al. (1995) in *Two-component signal transduction*, eds. Hoch and Silhavy (ASM, Washington, D.C.), pp. 25–51).

To assess the structural similarity of $BeF_x$-activated receiver domains to the corresponding phosphorylated domains, we used NMR spectroscopy to evaluate the changes in chemical shift that resulted from these two means of activation of NtrCr, CheY, and Spo0F. Chemical shifts for isotope-labeled proteins have been reported for the unmodified, inactive state of each protein (Volkman et al. (1995) *Biochemistry* 34, 1413–1424; Feher et al. (1997) *Biochemistry* 36, 10015–10025; Moy et al. (1994) *Biochemistry* 33, 10731–10742; Santoro et al. (1995) *J. Mol. Biol.* 247, 717–725), and they have also been determined for $P-NtrC^r$ and P-CheY (Lowry et al. (1994) *J. Biol. Chem.* 269, 26358–26362; Nohaile et al. (1997) *J. Mol. Biol.* 273, 299–316). Titrations of $NtrC^r$ and CheY with $BeCl_2$ and NaF produced new resonances in the slow exchange limit, coexisting with those of the inactive forms. By adjusting the concentrations of $Be^{2+}$, $F^-$ and $Mg^{2+}$, it was possible to convert the proteins quantitatively to $BeF_x$ complexes. Resonances from the $BeF_x.NtrC^r$ and $BeF_x$.CheY complexes were assigned using triple resonance 3D experiments on $C^{13}/N^{15}$ enriched proteins, making possible direct comparisons with the corresponding phosphorylated forms. The chemical shift differences between $BeF_x.NtrC^r$ and $NtrC^r$ were remarkably similar to those between $P-NtrC^r$ and $NtrC^r$ (FIG. 6), particularly for the residues that showed the largest changes. Although chemical shift changes are notoriously difficult to interpret directly, the correlation in the patterns argues strongly that very similar structural changes are likely to occur upon activation by either mechanism. In particular, it has been shown recently that there is a substantial reorganization of the face comprised of helices 3 and 4 and strands 4 and 5 in $P-NtrC^r$ and based on changes in chemical shift, the same is likely to be true in $BeF_x.NtrC^r$.

Figure 6:
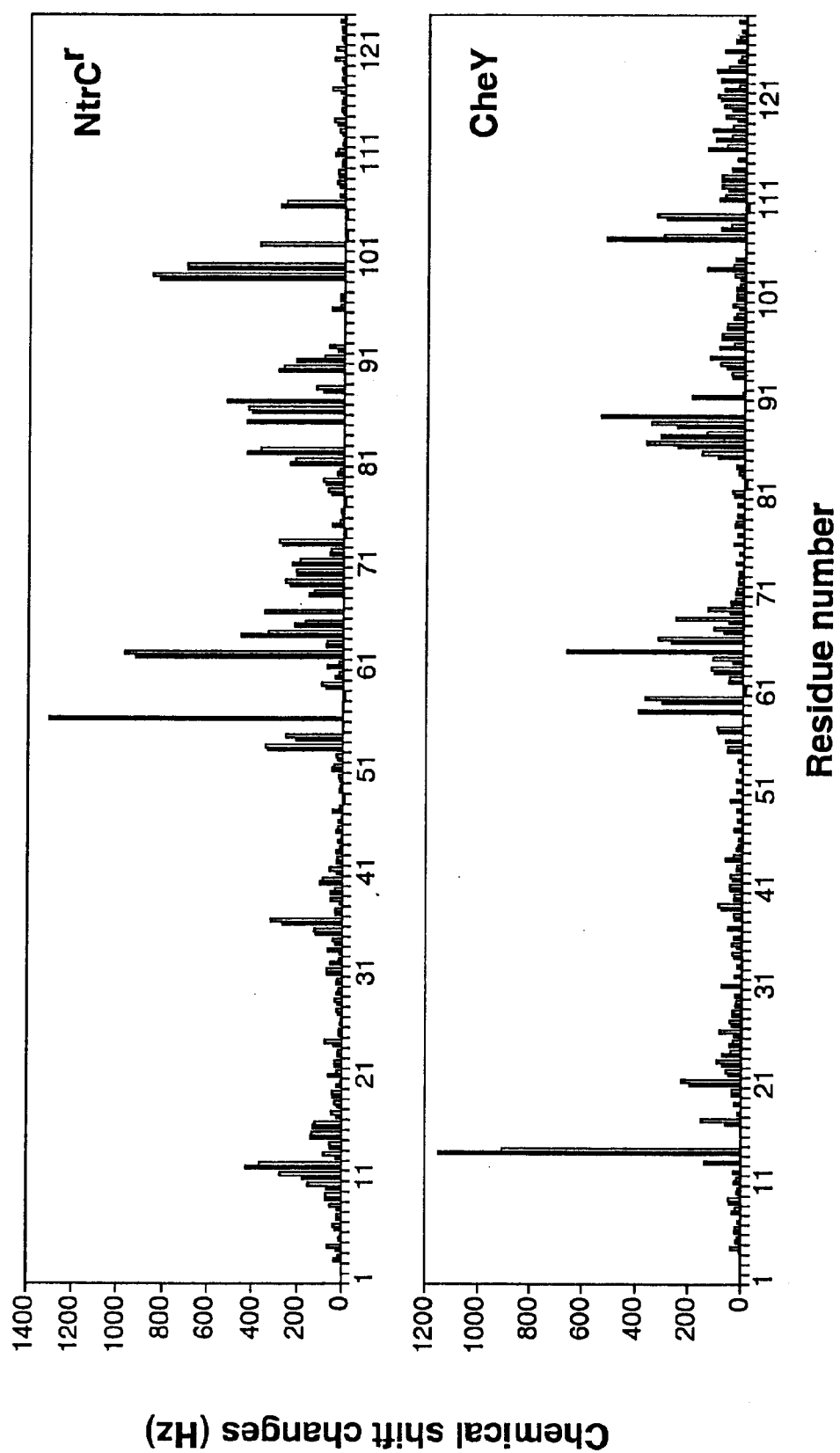
FIG. 6 is a graph showing the chemical shift changes of amide nitrogens and protons, $(\Delta\delta_N^2+\Delta\delta_H^2)^{1/2}$, with $\Delta\delta$ in Hz, upon activation of $NtrC^r$ or CheY. Solid bars indicate the difference between the $BeF_x$-activated and inactive states, whereas open bars do so for the phosphorylated and inactive states. Small negative bars designate proline residues, which have no NH.

Due to instability of the aspartyl phosphate, assignment of resonances for P-CheY was very difficult and the assignments are less complete than for unmodified CheY (Lowry et al. (1994) *J. Biol. Chem.* 269,26358–26362). Nevertheless, after correcting for one very likely misassigned resonance in P-CheY that shifts substantially (Lowry et al. (1994) *J. Biol. Chem.* 269, 26358–26362), profiles of the differences in chemical shift between $BeF_x$.CheY and CheY are very similar to those between P-CheY and CheY (FIG. 6). Thus, for both NtrC$^r$ and CheY, differences in chemical shift for the $BeF_x$ complexes recapitulate those for the corresponding phosphorylated (activated) forms.

For Spo0F, it has not yet been possible to achieve quantitative phosphorylation (Zapf et al. (1996) *Biochemistry* 35,2926–2933) and hence a comparison of NMR data for $BeF_x$.Spo0F and P-Spo0F cannot be made. However, several of the distinctive shifted resonances that show large changes upon activation of both NtrC$^r$ and CheY, show similar changes for $BeF_x$.Spo0F (data not shown). This provides evidence that it, too, is in an active state, although biochemical studies will be required to verify this.

Example 5

Refinement of the $BeF_3^-$.PSP Structure

Figure 8:
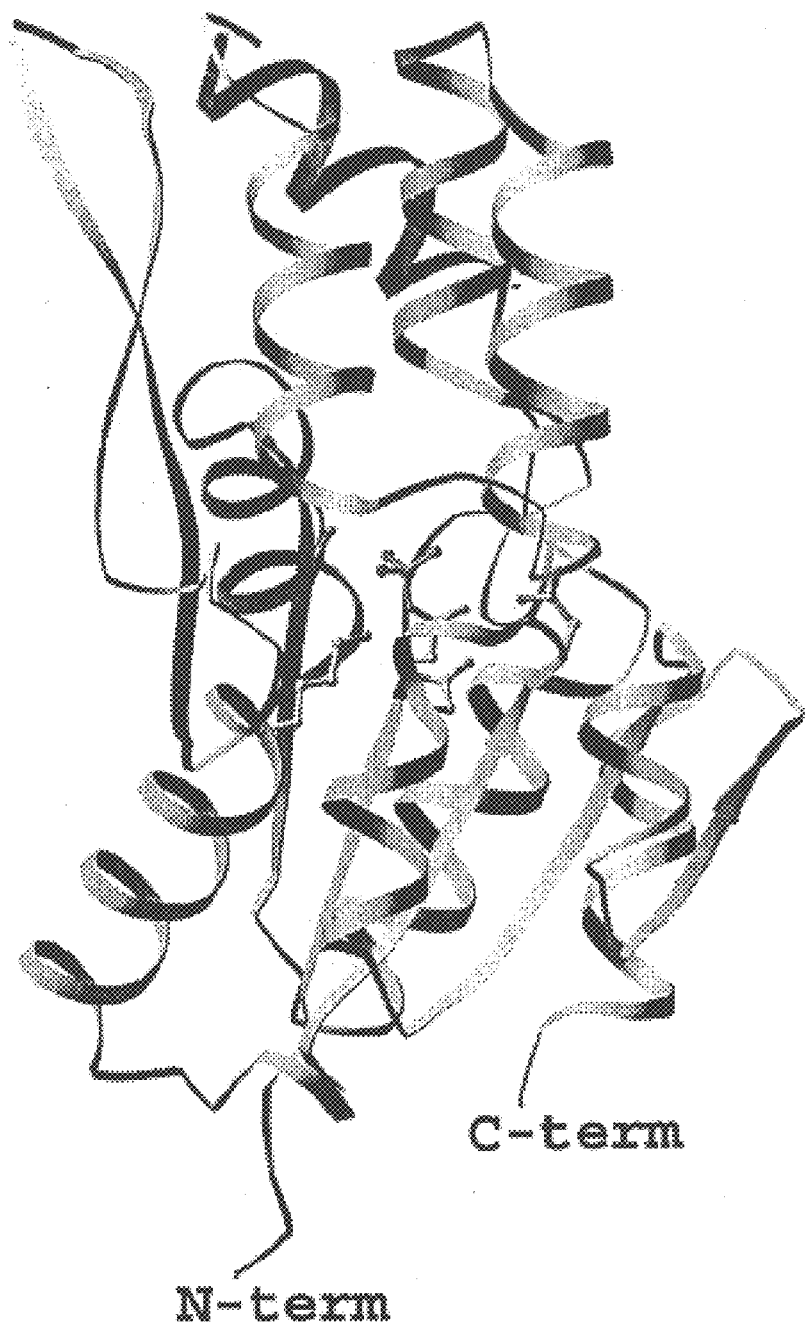
FIG. 8 is a ribbon diagram of $BeF_3^-$·PSP. The sidechains of highly conserved active site residues, Asp-11, Ser-99, Lys-144, Asp-167, and Asp-171, are shown in ball and stick form.

Refinement of the $BeF_3^-$. PSP crystal structure revealed that the overall topology of PSP is composed of two domains: a core $\alpha/\beta$ domain and a four-helix bundle domain that covers the active site (FIG. 8). $BeF_3^-$ is bound to Asp 11, the site of phosphorylation (Collet et al. (1998) *Journal of Biological Chemistry* 273, 14107–14112), and is surrounded by the sidechains of residues that are highly conserved in the HAD superfamily of proteins. The $BeF_3^-$.PSP crystal structure is very similar to a recently solved PSP structure that was found to contain a phosphate ($PO_4^{2-}$) in the active site.

Example 6

$BeF_3^-$.PSP Complex Formation

In our previous studies with $BeF_3^-$, NMR spectroscopy proved to be a convenient method for following complex formation with response regulators. Backbone amide $^1H$ and $^{15}N$ chemical shifts are sensitive to both the local structure and electronic environment; thus, changes in $^1H$-$^{15}N$ FHSQC crosspeak positions produced by the addition of $BeF_3^-$ are diagnostic of complex formation. Using NMR spectroscopy, we readily determined that in solution $BeF_3^-$ formed a persistent complex with PSP. For the response regulators CheY and NtrC$^r$, backbone amide chemical shift changes induced by $BeF_3^{-31}$ complex formation are similar to those induced by phosphorylation (Yan et al. (1999) *Proceedings of the National Academy of Sciences of the United States of America* 96, 14789–14794). Because PSP can not be maintained in a phosphorylated state long enough to perform a similar comparison (the reason for development of stable analogs in the first instance), no direct comparison could be made between the $BeF_3^-$ analog and the naturally occurring phosphorylated PSP.

Example 7

$BeF_3^-$ Inhibits the Activity of PSP

Figure 10:
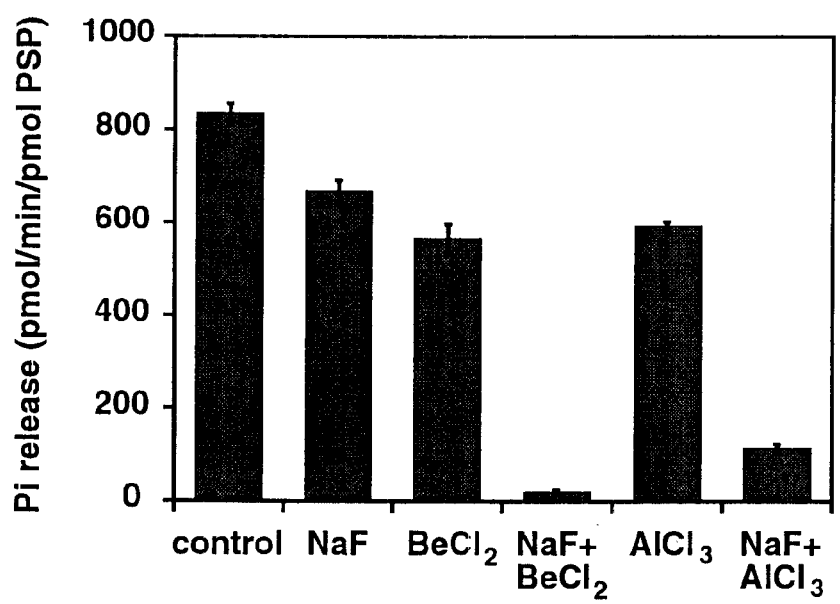
FIG. 10 is a graph showing the inhibition of PSP by $BeF_3^-$ and AlF. Standard deviations are shown by error bars.
Figure 11:
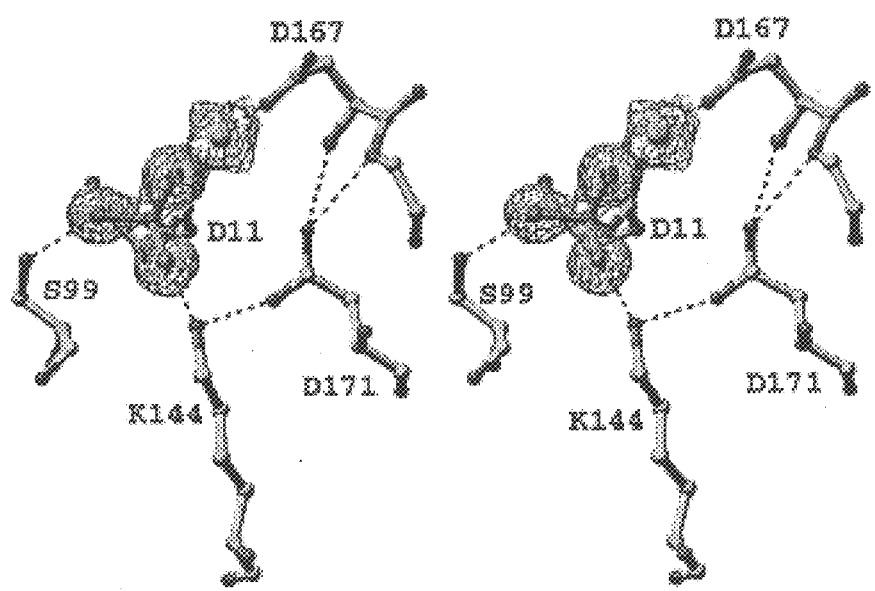
FIG. 11 is a stereoview of the $BeF_3^-$ PSP active site. The $2F_o$-$F_c$ electron density map covering the magnesium and fluorine atoms was calculated in the absence of these atoms and is shown contoured at 1 sigma. The dashed lines represent hydrogen bonds, salt bridges, and metal-ligand interactions. Three of the Mg2+ ligands, two water molecules and Asp 13-C=O, are not shown.

Previous biochemical experiments have shown that $BeF_3^-$ activates various response tregulators in a manner similar to phosphorylation (Yan, D., et al. (1999) *Proceedings of the National Academy of Sciences of the United States of America* 96, 14789–14794, Cho, H. S., et al., (2000) *Journal of Molecular Biology* 297, 543–551). If $BeF_3^-$ can also act as an aspartyl phosphate analog in PSP, it would inhibit the activity of PSP by preventing formation of the phosphoenzyme intermediate. As shown in FIG. 10, the hydrolytic activity of PSP was significantly inhibited in the presence of both NaF and $BeCl_2$. Neither alone had such a profound effect. As a thermostable enzyme, PSP from hyperthermophile *M. jannaschii* exhibited maximum activity at 70° C. The enzyme activity was similarly inhibited by $BeF_3^-$ at either 70° C. or room temperature (data not shown). Together with the NMR evidence, this shows that $BeF_3^-$ serves as an aspartyl phosphate analog in solution and forms a persistent complex with PSP mimicking the phosphoenzyme intermediate.

As shown in FIG. 10, aluminofluoride ($AlF_x$, generated in situ by mixing NaF and $AlCl_3$) can substitute for $BeF_3^-$ to inhibit PSP activity. In response regulator CheY, both biochemical and structural experiments have indicated that $AlF_x$ is also an aspartyl phosphate analog-activating CheY similar to phosphorylation or $BeF_3^-$. A third phosphate analog, orthovanadate ($VO_4^{3-}$), was also observed to inhibit PSP activity (data not shown) (Veeranna et al. (1990) *Neurochemical Research* 15, 1203–1210). The major difference among these phosphate analogs is their different geometries (Martin (1988) *Biochem. Biophys. Res. Commun.* 155, 1194–1200; Chabre (1990) *Trends Biochem. Sci.* 15, 6–10; Petsko (2000) *Proceedings of the National Academy of Sciences of the United States of America* 97, 538–540). $BeF_3^-$ is strictly a tetrahedral ground state analog of phosphate, whereas $AlF_x$ and $VO_4^{3-}$ are often seen as square planar transition state analogs of phosphate.

Example 8

Active Site of $BeF_3^-$.PSP

HAD family proteins that utilize a phospho-aspartate intermediate have a set of conserved all of residues that in PSP (MJ) correspond to Asp 11, Ser 99, Lys 144, Asp 167, and Asp 171. Mutation of any of these residues in human PSP, except Ser to Thr, dramatically decreases the catalytic efficiency (Collet et al. (1999) *Journal of Biological Chemistry* 274, 33985–33990). In the active site of $BeF_3^-$.PSP (FIG. 10), these conserved residues come together to form interactions with the aspartyl phosphate mimic ($BeF_3^-$) and/or the catalytically required divalent cation, $Mg^{2+}$. Asp 11-O$\delta$1 is bound to the beryllium (1.5 Å) of $BeF_3$. Asp 11-O$\delta$2, along with a fluorine, Asp 13-C=O, Asp 167-O$\delta$, and two water molecules occupy the six coordination sites of $Mg^{2+}$. Ser 99-O$\gamma$ forms a hydrogen bond with $BeF_3^-$. Lys 144-N$\zeta$ forms salt bridges with $BeF_3^-$ and Asp 171-O$\delta$1. Asp 171-O$\delta$2 forms hydrogen bonds with the backbone amides of Asp 167 and Gly 168. These two hydrogen bonds appear to stabilize the conformation of the backbone around Asp 167 such that the Asp 167 sidechain is restrained in a position to coordinate with $Mg^{2+}$.

Example 9

Comparison of $BeF_3^-$.PSP and $BeF_3^-$.CheY

Figure 12A:
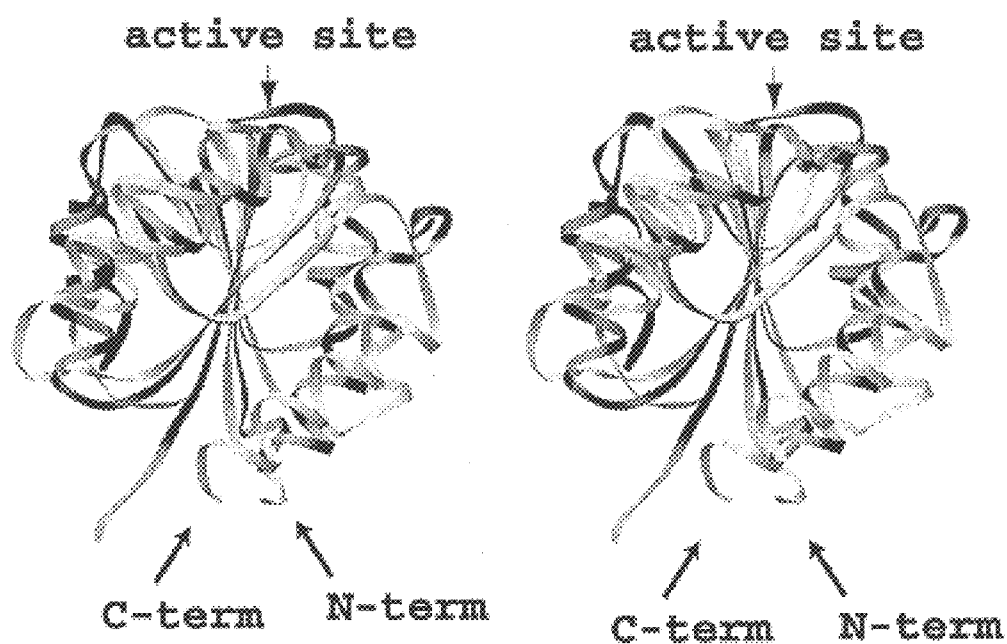
FIGS. 12A and 12B contain stereoviews showing the superposition of BeF$_3^-$-PSP and BeF$_3^-$-CheY (*E. coli*). Structurally homologous β-strand residues (PSP: 7 –11, 94–98, 116–120, 162–167, 180–182 and CheY: 8–13, 34–36, 53–57, 82–86, 104–108) were used for the superposition.
Figure 12B:
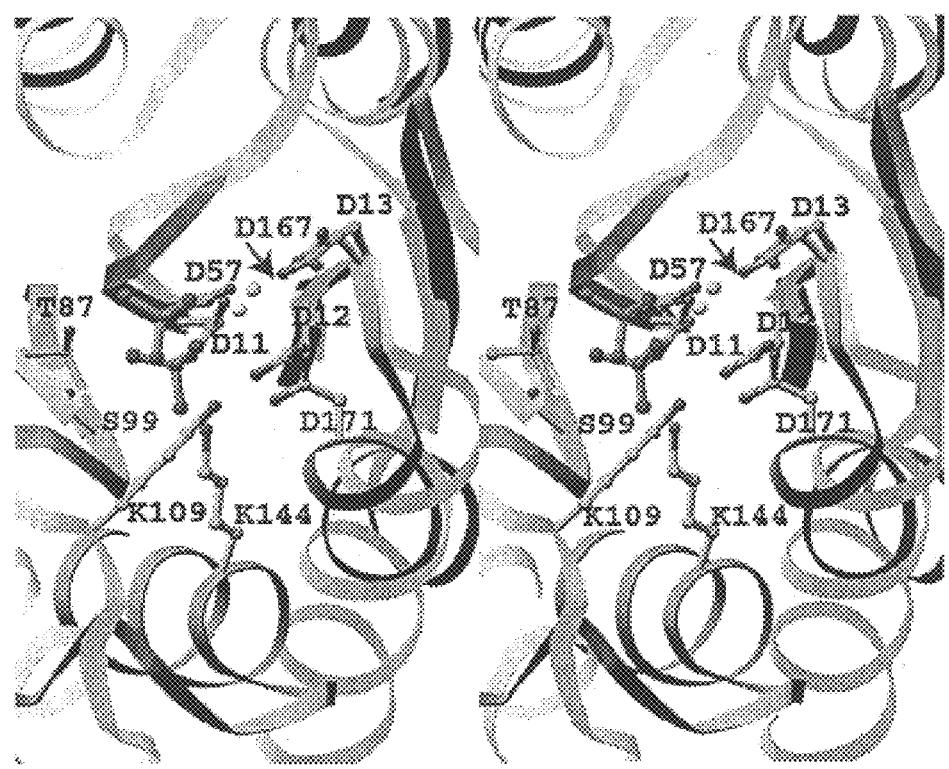

Response regulators and phosphotransferases in the HAD family share the same quintet of highly conserved residues, although a circular permutation is required to align the primary sequences. Superposition of the structurally homologous β-strand residues of $BeF_3^-$ PSP and $BeF_3^-$ CheY results in an r.m.s.d. of only 0.6 Å (FIG. 12A). The core β-sheets show a similar curvature, whereas the α-helices show a large degree of conformational variation The active sites reveal that the conserved residues of PSP and CheY form very similar hydrogen bonds, salt bridges, and ligand coordinations (FIG. 12B). PSP residues Asp 11, Ser 99, and Asp 167 are functionally and structurally equivalent to CheY residues Asp 57, Thr 87, and Asp 13, respectively. Although PSP residues Lys 144 and Asp 171 appear to be functionally equivalent to CheY residues Lys 109 and Asp 12, these sidechains originate from different structural elements. Lys 144 (PSP) is anchored to an α-helix, whereas Lys 109 (CheY) is anchored to a loop. Nevertheless, the functional groups of both lysine residues reach comparable positions in the active site and form salt bridges with $BeF_3^-$ and an aspartate residue, Asp 171 (PSP) and Asp 12 (CheY). Asp 171 (PSP) is anchored to an α-helix, whereas Asp 12 (CheY) is anchored to the c-terminus of a β-strand.

Considering that the pairs of aspartate residues, Asp 167 and Asp 171 of PSP and Asp 12 and Asp 13 of CheY, hold such different relative positions in the primary sequence, there is a surprising amount of similarity in how these residues are chemically and structurally involved in $Mg^{2+}$ coordination (FIG. 12B). In PSP, the first residue (in the primary sequence) of the pair, Asp 167, acts as a direct ligand to $Mg^{2+}$, whereas in CheY it is the second, Asp 13. Asp 167 (PSP) and Asp 13 (CheY) are both located in similarly structured loops that are stabilized by hydrogen bonds from the other aspartate of the respective pairs. In addition to stabilizing the loops, Asp 171 (PSP) and Asp 12 (CheY) form salt bridges with the highly conserved lysine residue, Lys 144 (PSP) and Lys 109 (CheY). This salt bridge, in both proteins, appears to be important for positioning the loop containing the aspartate that serves as a $Mg^{2+}$ ligand in the active site. In the catalytic domain of the $Ca^{2-}$ P-type ATPase, the homologous pair of aspartate residues (Asp 703 and Asp 707) forms a similar loop structure that allows $Mg^{+2}$ binding. The aspartate that functions as a direct $Mg^{2+}$ ligand is not conserved in HAD family proteins that do not require a divalent cation for activity (Aravind et al. (1998) *Trends in Biochemical Sciences* 23, 127–129; Koonin et al. (1994) *Journal of Molecular Biology* 244, 125–132).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A modified polypeptide comprising an acyl phosphate analogue comprising a fluorinated beryllium atom, with the proviso that the polypeptide is not a CaATPase.

2. The modified polypeptide of claim 1, wherein the polypeptide is a response regulator polypeptide.

3. The modified polypeptide of claim 1, wherein the polypeptide is selected from the group consisting of phosphotransferases, phosphatases, phosphomutases, and P-type ATPase.

4. The modified polypeptide of claim 1, wherein the acyl phosphate analogue is an aspartyl phosphate analogue.

5. The modified polypeptide of claim 1, wherein the modified polypeptide is functionally active.

6. A modified response regulator polypeptide comprising an aspartyl phosphate analog comprising a fluorinated beryllium atom, with the proviso that the polypeptide is not a CaATPase.

7. The modified response regulator polypeptide of claim 6, wherein the modified response regulator polypeptide is functionally active.

8. A modified polypeptide comprising an acyl phosphate analogue comprising a fluorinated beryllium atom, wherein the modified polypeptide is selected from the group consisting od phosphotransferases, phosphatases, phosphomutases, and P-type ATPase, with the proviso that the polypeptide is not a CaATPase.

9. The modified polypeptide of claim 8, wherein the modified polypeptide is functionally active.

10. A functionally active modified polypeptide comprising an acyl phosphate analogue comprising a fluorinated beryllium atom.

11. The modified polypeptide of claim 10, wherein the polypeptide is a response regulator polypeptide.

12. The modified polypeptide of claim 10, wherein the polypeptide is selected from the group consisting of phosphotransferases, phosphatases, phosphomutases, and P-type ATPase.

13. The modified polypeptide of claim 10, wherein the acyl phosphate analogue is an aspartyl phosphate analogue.

14. A functionally active modified response regulator polypeptide comprising an aspartyl phosphate analog comprising a fluorinated beryllium atom.

15. A functionally active modified polypeptide comprising an acyl phosphate analogue comprising a fluorinated beryllium atom, wherein the functionally active modified polypeptide is selected from the group consisting of phosphotransferases, phosphatases, phosphomutases, and P-type ATPase.

* * * * *